United States Patent [19]
Hovland et al.

[11] Patent Number: 6,015,393
[45] Date of Patent: Jan. 18, 2000

[54] SYSTEMS AND METHODS FOR MONITORING AND EVALUATING PENILE TUMESCENCE

[75] Inventors: Claire T. Hovland, Minnetonka, Minn.; Roger Dixon, Bothell, Wash.; L. Dean Knoll, Brentwood, Tenn.; Jerome H. Abrams, St. Paul, Minn.

[73] Assignee: UroMetrics, Inc., St. Paul, Minn.

[21] Appl. No.: 09/045,599

[22] Filed: Mar. 20, 1998

Related U.S. Application Data

[60] Provisional application No. 60/041,684, Mar. 24, 1997, and provisional application No. 60/064,305, Nov. 5, 1997.

[51] Int. Cl.$^7$ .................................................. A61B 5/103
[52] U.S. Cl. ........................ 600/587; 600/504; 600/506; 600/507; 607/143; 346/33 ME
[58] Field of Search ..................................... 600/587, 507; 346/34, 76 R, 33 ME; 33/179; 607/143; 514/11

[56] References Cited

U.S. PATENT DOCUMENTS

| | | |
|---|---|---|
| 4,103,678 | 8/1978 | Karacan et al. . |
| 4,428,385 | 1/1984 | Morales . |
| 4,469,108 | 9/1984 | Goldstein . |
| 4,515,166 | 5/1985 | Timm . |
| 4,572,211 | 2/1986 | Sagalowsky . |
| 4,606,353 | 8/1986 | Timm . |
| 4,747,415 | 5/1988 | Lavoisier . |
| 4,766,909 | 8/1988 | Trimm et al. . |
| 4,848,361 | 7/1989 | Penney et al. . |
| 4,911,176 | 3/1990 | Timm et al. . |
| 4,928,706 | 5/1990 | Trick . |
| 5,284,153 | 2/1994 | Raymond et al. . |
| 5,576,290 | 11/1996 | Hadley ....................................... 514/11 |

OTHER PUBLICATIONS

Sexson, M.D., W.R., et al., "Cardiothoracic Variables Measured by Bioelectrical Impedance in Preterm and Term Neonates," Critical Care Medicine, vol. 19, No. 8, pp. 1054–1059, 1991.

Chen, K.K. et al., "Sonographic Measurement of Penile Erectile Volume," Journal of Clinical Ultrasound, vol. 20, pp. 247–253, 1992.

Zuckier, L.S., et al., "A Nonimaging Scintillation Probe to Measure Penile Hemodynamics," Journal of Nuclear Medicine, vol. 36, No. 12, pp. 2345–2351, Dec. 1995.

RigiScan® Plus, Rigidity Assessment System, Osbon Medical Systems brochure, 1996.

Nyboer, Jan, et al., "Quantitative Studies of Electrical Conductivity of the Peripheral Body Segments," Annals of Western Medicine and Surgery, vol. 5, No. 1, pp. 11–20, Jan., 1951.

(List continued on next page.)

Primary Examiner—Marvin M. Lateef
Assistant Examiner—Ali M. Imam
Attorney, Agent, or Firm—Patterson & Keough, P.A.

[57] ABSTRACT

An apparatus for monitoring the tumescent state of the penis of a patient includes a plurality of sensing elements to be placed in proximity to the penis for sensing penile impedance values. A processing device is operably coupled to the plurality of sensing elements, the processing device determining at least one penile variable using the impedance values. The at least one penile variable is selected from the group consisting of length, volume, volume-change, cross-sectional area and volume-filling rate variables. An output device operably coupled with the processing device to generate a display using the at least one determined penile variable. The output device displays e.g. a plot of penile length, penile volume values and/or penile cross-sectional area values for comparison by a user of the apparatus, readily allowing the user to distinguish artifactual effects from erectile events. According to one embodiment, cardiac-signature data is determined using the penile impedance values, and the apparatus indicates periods of erectile activity using the cardiac-signature data. Corresponding methods also are discussed.

49 Claims, 31 Drawing Sheets

OTHER PUBLICATIONS

Kubicek, W.G., PhD., et al., "Development and Evaluation of an Impedance Cardiac Output System," Aerospace Medicine, pp. 1208–1212, Dec. 1966.

Geddes, L.A., et al., "The Specific Resistance of Biological Material—A Compendium of Data for the Biomedical Engineer and Physiologist," Medical and Biological Engineering, vol. 5, pp. 271–293, 1967.

Nyboer, J., Electrical Impedance Plethysmography, Springfield: Charles C. Thomas. pp. 3–38, 1970.

Kubicek, W.G., et al., "The Minnesota Impedance Cardiograph—Theory and Applications," Biomedical Engineering, vol. 9, pp. 410–417, Sep. 1974.

Woodcock, J.P., "Plethysmography," Biomedical Engineering, pp. 406–409, Sep. 1974.

Quail, A.W., et al., "Thoracic Resistivity for Stroke Volume Calculation in Impedance Cardiography," J. Appln. Physiol. vol. 50, pp. 191–195, 1981.

Schmidt, H.S., et al., "Significance of Impaired Penile Tumescence and Associated Polysomnographic Abnormalities in the Impotent Patient," The Journal of Urology, vol. 126, pp. 348–352, 1981.

Bennett, A.H., M.D., "Arterial and Venous Hemodynamics in Male Impotence," Management of Male Impotence, vol. 5, pp. 108–126, 1982.

Kedia, K.R., "Vasculogenic Impotence: Diagnosis and Objective Evaluation Using Quantitative Segmental Pulse Volume Recorder," British Journal of Urology, vol. 56, pp. 516–520, 1984.

"NCCOM 3 Cardiovascular Monitor Operator's Manual," BoMed® Medical Manufacturing Limited, 1984.

Bradford, J.M.W., "The Use of a Bioimpedance Analyzer in the Measurement of Sexual Arousal in Male Sexual Deviants," Can. J. Psychiatry, vol. 31, Feb. 1986.

Bernstein, D.P., M.D., "Continuous Noninvasive Real–Time Monitoring of Stroke Volume and Cardiac Output by Thoracic Electrical Bioimpedance," Critical Care Medicine, vol. 14, No. 10, pp. 898–901, 1986.

Bernstein, D.P., M.D., "A New Stroke Volume Equation for Thoracic Electrical Bioimpedance: Theory and Rationale," Critical Care Medicine, pp. 904–909, 1986.

Appel, P.L., et al., "Comparison of Measurements of Cardiac Output by Bioimpedance and Thermodilution in Severly Ill Surgical Patients," Critical Care Medicine, vol. 14, No. 11, pp. 933–935, 1986.

de Mey, C., M.D., et al., "Noninvasive Assessment of Cardiac Performance by Impedance Cardiography: Disagreement Between Two Equations to Estimate Stroke Volume," Aviation, Space, and Environmental Medicine, pp. 57–62, Jan. 1988.

Preiser, J.C., et al., "Transthoracic Electrical Bioimpedance Versus Thermodilution Technique for Cardiac Output Measurement During Mechanical Ventilation," Intensive Care Medicine, vol. 15, pp. 221–223, 1989.

Nelson, R.P., et al., "Determination of Erectile Penile Volume by Ultrasonography," The Journal of Urology, vol. 141, pp. 1123–1126, 1989.

Wong, D.H., M.D., et al., "Noninvasive Cardiac Output: Simultaneous Comparison of Two Different Methods with Thermodilution," Anesthesiology, vol. 72, No. 5, pp. 781–792, 1990.

FIG. 8
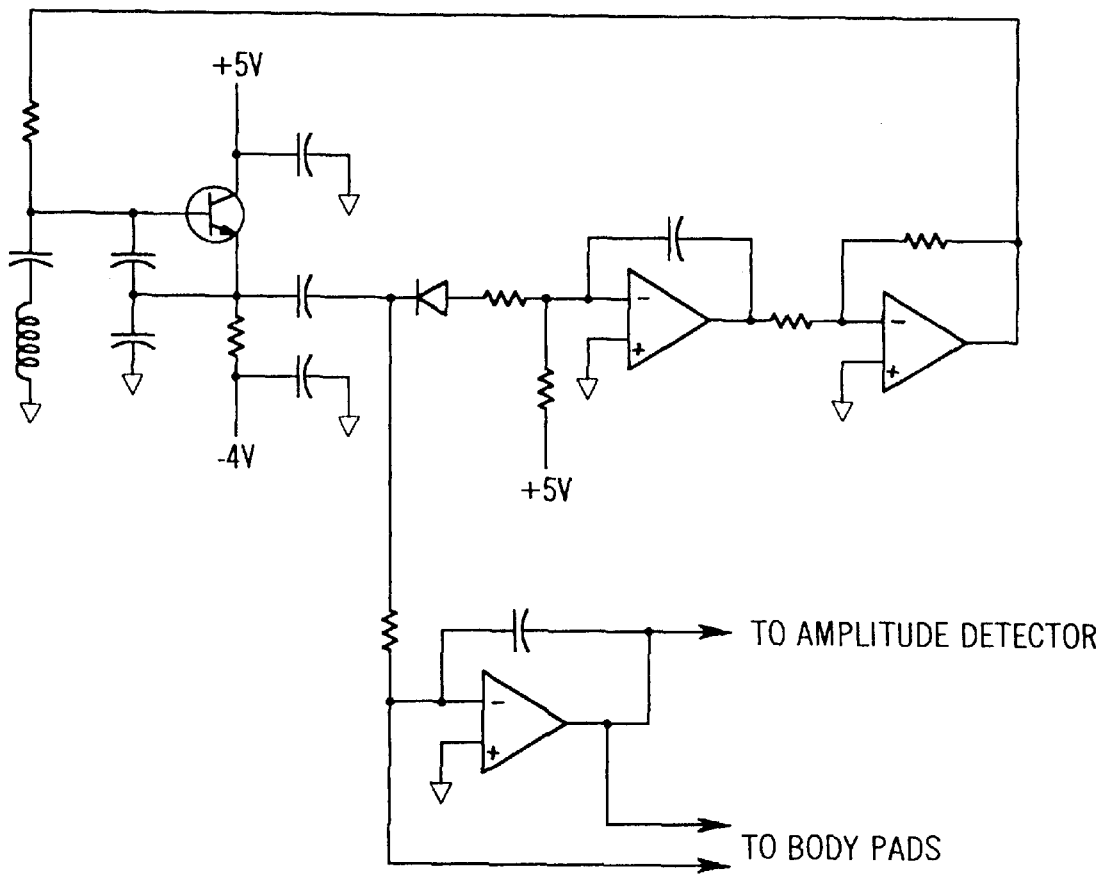
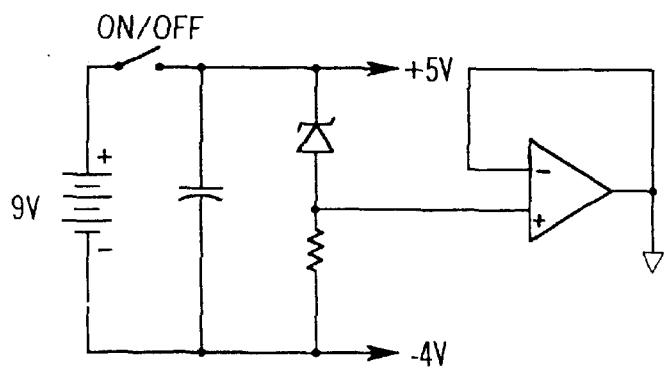
CONSTANT-AMPLITUDE OSCILLATOR/CURRENT SOURCE/
POWER SUPPLY

AMPLITUDE DETECTOR FLOWPASS FILTER/ANALOG
TO DIGITAL CONVERTER

WAVEFORM MEMORY

FIG. 23
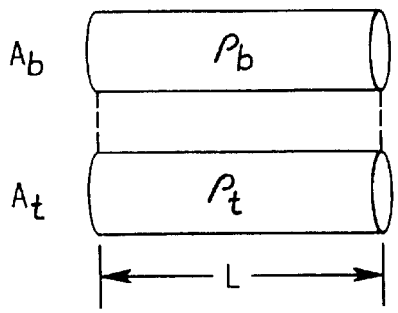
PENILE DECOMPOSITION INTO
BLOOD AND TISSUE FILLED REGIONS
FIG. 24
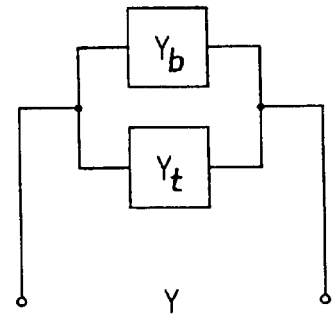
EQUIVALENT CIRCUIT
FIG. 25
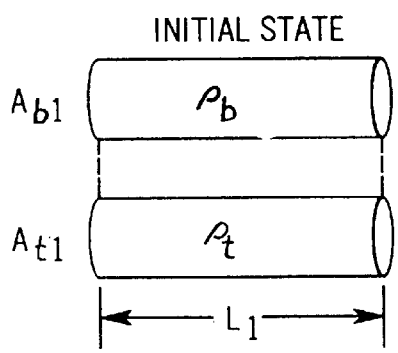          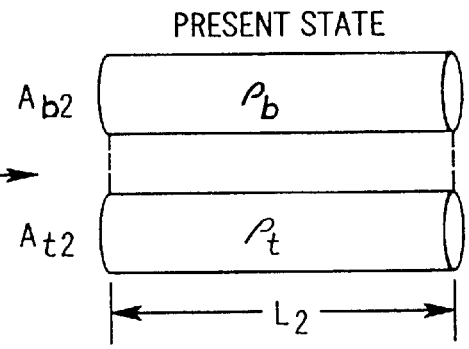
INITIAL STATE                 PRESENT STATE
FIG. 26
EQUIVALENT CIRCUITS
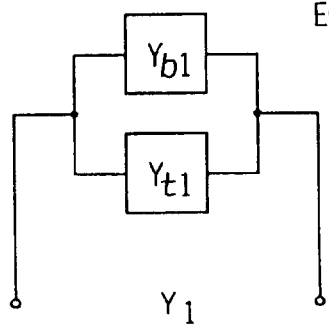          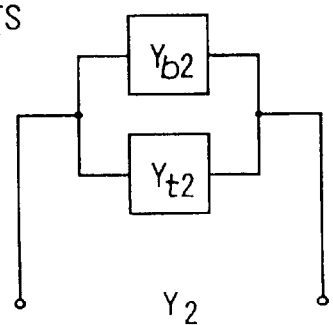
$Y_1$                         $Y_2$ CATACROTIC LIMB OF PULSE WAVE: (A) NORMAL CURVE: NET AREA NEGATIVE
(B) ABNORMAL CURVE: NET AREA POSITIVE

DICROTIC NOTCH: (A) PRESENT IN NORMAL CURVE (B) ABSENT IN ABNORMAL CURVE

SYSTEMS AND METHODS FOR MONITORING AND EVALUATING PENILE TUMESCENCE

CROSS-REFERENCE TO RELATED APPLICATIONS

The subject matter of this application is related to the subject matter of commonly assigned U.S. Provisional patent application Ser. Nos. 60/041,684, filed Mar. 24, 1997, and 60/064,305, filed Nov. 5, 1997, priority to which is claimed under 35 U.S.C. § 119(e) and which are incorporated herein by reference in their entirety.

BACKGROUND OF THE INVENTION

1. Field of the Invention

The invention relates to devices and methods for monitoring erectile events, and more particularly, for using penile impedance values in monitoring and evaluating nocturnal and diurnal erectile events for distinguishing between and/or diagnosing organic and psychogenic erectile dysfunction.

2. Description of Related Art a. Erectile Dysfunction

Male impotence is defined as the chronic inability to attain and/or maintain an erection of sufficient rigidity for sexual intercourse. This problem affects approximately 30 million American men, with increasing incidence in those of advanced age. Impotence is a source of great anxiety for many and is the subject of many thousands of visits to physicians and other medical professionals every year.

During a normal erection, neurochemical stimulation causes penile arterial inflow to increase in each cavemosal artery. The result is increased blood flow into the corpora cavernosa. The subtunical venous plexus is compressed against the tunica albuginea, and venous outflow is reduced to trap blood in the corpora cavernosa. This combination of increased inflow and decreased outflow results in vascular congestion of the penis, tumescence, and rigidity sufficient for sexual intercourse.

It is believed that abnormal reduction of blood flow through the cavernosal arteries and/or excess venous outflow, i.e. corporal venous leakage, are the primary organic causes of vasculogenic impotence. These abnormal blood-flow characteristics through the cavernosal arteries can be caused by a number of factors, for example, diabetes, atherosclerotic vascular disease, traumatic arterial occlusive disease, or defective veno-occlusive mechanisms.

Erectile dysfunction can also originate in the mind, involving mental or emotional processes, i.e. it can have a psychological rather than physiological origin. Psychogenic causes include depression, anger/tension, low self-esteem, and fear. Additionally, organic impotence also often acquires a psychogenic component over time. Whether a patient's impotence is of organic or purely psychogenic origin, of course, determines the course of treatment.

b. Nocturnal Tumescence Monitoring

It is generally believed that patients with purely psychogenic impotence achieve normal erections nocturnally. Patients with organic impotence, on the other hand, generally suffer impaired erectile performance both nocturnally and while awake. Thus, measurement of nocturnal penile tumescence is a known technique for distinguishing between impotence of psychogenic and organic origin. Various devices and methods for performing nocturnal measurements have been developed.

One such method and device is disclosed in U.S. Pat. No. 4,515,166 to Timm, which is incorporated herein by reference. The disclosed apparatus, believed to be marketed as the RIGISCAN PLUS rigidity assessment system by Imagyn Medical Technologies, Inc., includes a number of loop-like structures that are positioned around the circumference of the penis. Periodically while the patient sleeps, a torque motor and an associated sprocket drive assembly exert a calibration force on the loop-like structures. Displacement of a cable connected to the loops while the torque motor is repetitively activated provides an output function that correlates to the compressibility or rigidity of the penis. Following a series of measurements, two-dimensional or three-dimensional graphic outputs of time versus tumescence can be created.

Another system for measuring nocturnal penile tumescence includes one or more mercury strain-gauge transducers. A loop-shaped tubing is filled with mercury and positioned around the patient's penis. As penile circumference changes, electrical circuitry detects changes in resistance values of the strain gauges to provide a rough indication of tumescence.

Another, even-less-precise method of monitoring nocturnal penile tumescence involves placing a ring of postage-type stamps snugly around the penis shortly before sleep. Upon awakening, the patient inspects the ring to determine whether any of the stamps are separated from each other, that is, whether the stamp ring has been broken. Although providing limited data, this method has certain advantages over merely subjective evaluations of nocturnal erectile activity.

Various penile tumescence monitoring devices and methods are disclosed in U.S. Pat. Nos. 4,469,108, 4,766,909, 4,747,415, 4,928,706, 4,428,385, 4,848,361, and 4,911,176, which are incorporated herein by reference.

c. Disadvantages of Current Monitoring Devices

Prior art methods and devices, however, suffer a number of significant disadvantages. Devices that surround the penis with constricting loops and then subject the loops to periodic, motor-induced tensioning may be viewed as somewhat intrusive and uncomfortable. Additionally, electronic-type monitoring devices are often of significant size, mass or volume, again contributing to patient discomfort and potential sleeplessness. Such devices also make travel impractical, possibly requiring an overnight stay in a medical facility for nocturnal monitoring and therefore causing significant inconvenience and expense to the patient and potentially interfering with nocturnal erectile performance. They also generally have significant power requirements and often provide only an indication of circumference at specific, spaced time-points.

Purely manual devices, of course, also fail to provide sufficient data for thorough evaluation and/or analysis; indeed, many prior art manual devices are so-called "one-shot" devices that merely indicate whether an erection has occurred, without providing more information.

In view of these disadvantages, a need has arisen for a monitoring and/or evaluation system of reduced size and otherwise unobtrusive construction, that provides enhanced data and more thorough evaluation and diagnosis capabilities.

d. Plethysmography—Introduction

Plethysmography is a known method for measuring blood flow/volume in the human body, most typically in the thoracic cavity. Various types of plethysmography are known, including volume-displacement plethysmography, strain-gauge plethysmography, segmental plethysmography, photoelectric plethysmography, and impedance plethysmography. These and other plethysmography devices and methods are described, for example, in Woodcock, J. P., "Plethysmography," *Biomedical Engineering*, September 1974, pp. 406–409, which is incorporated herein by reference.

e. Impedance Plethysmography

With impedance plethysmography, a constant, alternating current is caused to flow between electrodes spaced along the thoracic cavity, and a voltage drop between the electrodes is determined and correlated to impedance, or more specifically, bioimpedance. Tissue bioimpedance changes with variations in blood flow through the cavity. Various theories attempt to explain why this is so. According to one such theory, for example, bioimpedance changes over the cardiac cycle are due to the changing number of ions in the cavity when arterial inflow exceeds the rate of venous drainage. Other theories suggest that differing blood velocities or pressures, vessel distensibility, and/or orientation of red blood corpuscles contribute to bioimpedance changes. Typically, ventricular ejection causes an increase in blood volume and velocity, and corresponding changes in bioimpedance.

Both two-electrode and four-electrode impedance plethysmography techniques are known, for example as disclosed in Kubicek, W. G., et al., "The Minnesota Impedance Cardiograph—Theory and Applications," *Biomedical Engineering*, September 1974, pp. 410–417, which is incorporated herein by reference.

With the four-electrode technique, four aluminumized mylar strip electrodes are placed about the thoracic cavity of a patient—two electrodes generally in the neck region, one electrode at about the mid-point of the chest, and one electrode generally below the rib cage of the patient. The two outer electrodes supply constant, sinusoidal alternating current of 4 mA rms at 100 kHz longitudinally through the thorax of the patient. The two inner electrodes measure the potential difference between them along the thorax. More specifically, the product of the sinusoidal alternating current multiplied by the thoracic impedance generates a voltage between the inner electrodes, which is picked up by a high-input impedance linear amplifier. Outputs from the associated instrumentation include Z, which is the total impedance between the inner electrodes, $\Delta Z$, which is the impedance change during the cardiac cycle, and $dZ/dt$, which is the first derivative of $\Delta Z$ with respect to time. Generally speaking, Z is related to tissue volume and $dZ/dt$ is proportional to stroke volume, corresponding to the bolus of blood injected per heartbeat.

According to two-electrode applications of impedance plethysmography, a constant current passes through the thoracic cavity via the two electrodes. Potential drop across the electrodes is measured, and impedance between the electrodes is calculated based on the known current. Two-electrode impedance plethysmography is disadvantageous in that current distribution near the electrodes is not known precisely, and thus neither is the precise volume through which the current flows. Also, the impedance of the electrodes is added into the measurement, thereby biasing any calculation made with the impedance value itself. In four-electrode impedance plethysmography, on the other hand, current tends to spread homogeneously through the tissue, enabling more exact measurement.

f. Correlation of Impedance to Volume

Various equations have been proposed to correlate absolute volume and/or stroke volume per heartbeat with a bioimpedance variable. For example, from Bernstein, Donald P., "A New Stroke Volume Equation for Thoracic Electrical Bioimpedance: Theory and Rationale," *Critical Care Medicine*, 1986, pp. 904–909, and/or "NCCOM 3 Cardiovascular Monitor Operator's Manual," BoMed® Medical Manufacturing Limited, 1984, both of which are incorporated herein by reference, the following equation is derivable to determine thoracic stroke volume:

$$SV_{bi} = \frac{L^3 \cdot VET_{bi} \cdot (dZ/dt)_{max}}{4.2 \cdot Z_0}$$

where: $SV_{bi}$=bioimpedance stroke volume (cm³);
L=thoracic length, value from a nomogram that adjusts for deviations from ideal body weight and/or proportion (cm);
$VET_{bi}$=ventricular ejection time by bioimpedance (seconds);
$(dZ/dt)_{max}$=maximum rate of impedance change ($\Omega$/second); and
$Z_0$=baseline impedance ($\Omega$).

The Kubicek article referenced above also proposes a relationship between ventricular stroke volume and thoracic impedance change, according to the following equation:

$$SV = \left(\rho\left(\frac{L}{Z_0}\right)\right)^2 (T(dZ/dt))_{min}$$

Where: SV=ventricular stroke volume (cc);
$\rho$=electrical resistivity of blood at 100 kHz, average value is 150 ohm-cm;
L=mean distance measured between two (inner) electrodes (cm);
$Z_0$=the mean thoracic impedance between two (inner) electrodes in ohms;
$(dZ/dt)_{min}$=minimum value of $dZ/dt$ occurring during the cardiac cycle in ohms/second; and
T=ventricular ejection time in seconds, as obtained from the $dZ/dt$ waveform or from heart sounds.

The above equations assume constant thoracic circumference and/or volume. In the penile environment, on the other hand, circumference and volume are subject to significant change.

Kubicek also presents a derived formula to measure limb volume change without the use of a resistivity constant:

$$\Delta V = \frac{C^2 L}{4\pi Z_0}(\Delta Z)$$

where: C=average circumference of limb segment under measurement, in cm;
L=distance between measuring electrodes, in cm;
$Z_0$=mean impedance between the measuring electrodes, in ohms;
$\Delta Z$=impedance change during each heart beat, in ohms; and
$\Delta V$=volume change, in cm³.

Pulsatile limb blood flow then equals the product of $\Delta V$ and heart rate. Kubicek indicates that the above formula can be used in cuff-inflation venous-occlusion impedance plethysmography, in which case $Z_0$ is the initial impedance before venous occlusion and $\Delta Z$ is total impedance change between inflation and release of the cuff. Limb blood flow in ml/min equals $\Delta V/\Delta T \times 60$, where $\Delta T$ is the time between inflation and release of the cuff, in seconds.

The above equation assumes constant length, which of course is an invalid assumption in the penile environment during an erectile event. Additionally, venous occlusion by cuff inflation in the penile environment is generally impractical, especially in a nocturnal monitoring situation.

Other equations relating impedance to stroke volume, cardiac output or other volume indicators have been proposed and will be available to those of ordinary skill in the art. Additionally, the following articles provide additional background information and are incorporated herein by reference:

Appel, Paul L., et al. "Comparison of measurements of cardiac output by bioimpedance and thermodilution in severely ill surgical patients." *Critical Care Medicine*, Vol. 14, No. 11, pp. 933–935,1986;

Bennett, Alan H., M.D., "Arterial and Venous Hemodynamics in Male Impotence," *Management of Male Impotence*, Vol. 5, pp. 108–126, 1982;

Bernstein, Donald P., M.D. "Continuous noninvasive realtime monitoring of stroke volume and cardiac output by thoracic electrical bioimpedance," *Critical Care Medicine*, Vol. 14, No. 10, pp. 898–901, 1986;

Chen, K. K., et al., "Sonographic Measurement of Penile Erectile Volume," *J. Clin. Ultrasound*, Vol. 20, pp. 247–253, 1992;

de May, C., M.D., et al. "Noninvasive Assessment of Cardiac Performance by Impedance Cardiography: Disagreement Between Two Equations to Estimate Stroke Volume," *Aviation, Space, and Environmental Medicine*, January, 1988, pp. 57–62;

Kedia, K. R., "Vasculogenic Impotence: Diagnosis and Objective Evaluation Using Quantitative Segmental Pulse Volume Recorder," *British Journal of Urology*, Vol. 56. pp. 516–520, 1984;

Kubicek, W. G., et al., "The Minnesota Impedance Cardiograph—Theory and Applications," *Biomed. Eng.*, Vol. 9, pg. 410, 1974;

Nelson, R. P., et al., "Determination of Erectile Penile Volume by Ultrasonography," *The journal of Urology*, Vol. 141, pp. 1123–1126, 1989;

Nyboer, J., *Electrical Impedance Plethysmography Springfield*, Charles C. Thomas, p. 7, 1970;

Nyboer, Jan, et al., "Quantitative Studies of Electrical Conductivity of the Peripheral Body Segments," *Annals of Western Medicine and Surgery*, Vol. 5, No. 1, pp. 11–20, January, 1951;

Preiser, J. C., et al. "Transthoracic electrical bioimpedance versus thermodilution technique for cardiac output measurement during mechanical ventilation," *Intensive Care Medicine*, Vol. 15, pp. 221–223, 1989;

Quail, A. W., et al., "Thoracic Resistivity for Stroke-Volume Calculation in Impedance Cardiography," *J. Appln Physiol.*, Vol. 50, pp. 191–195, 1981;

Schmidt, H. S. et al., "Significance of Impaired Penile Tumescence and Associated Polysomnographic Abnormalities in the Impotent Patient," *The Journal of Urology*, Vol. 126, pp. 348–352, 1981;

Sexson, William R., M.D., et al., "Cardiothoracic variables measured by bioelectrical impedance in preterm and term neonates," *Critical Care Medicine*, Vol. 19, No. 8, pp. 1054–1059, 1991;

Wong, David H., M.D., et al. "Noninvasive Cardiac Output: Simultaneous Comparison of Two Different Methods with Thermodilution." *Anesthesiology*, Vol. 72, No. 5, pp. 784–792, 1990; and Zuckier, Lionel S., et al. "A Nonimaging Scintillation Probe to Measure Penile Hemodynamics," *Journal of Nuclear Medicine*, December, 1995, Vol. 36, No. 12, pp. 2345–2351.

g. The Difficulties of Using Impedance Plethysmography in the Penile Environment As mentioned above, impedance plethysmography has been used primarily in the thoracic environment, e.g. with two electrodes in the neck area and two electrodes at the mid and lower chest, as in the Kubicek article referenced above. The penile environment presents special problems, however, making it far more difficult to minimize artifactual effects than in the thoracic environment. (In fact, the difficulties in the penile environment have caused some to theorize that plethysmographic techniques in general can never be used in penile environments adequately to measure and evaluate erectile activity.)

Thoracic impedance plethysmography, for example, generally does not concern itself with significant size changes of the external thoracic cavity. The size of the penis significantly changes during an erectile event, however, by up to several times in circumference, length and/or volume. These increases in size cause increases in penile impedance, due e.g. to the changes in length, and therefore cause deviation from the thoracic model. Electrode spacing in the penis also is subject to change. Further, the skin of the penis moves even in the absence of an erectile event, making adequate electrical contact more of an issue. Additionally, patient movement and/or movement of the penis relative to the remainder of the patient's body also cause artifactual effects. These considerations are especially disadvantageous and confusing in nocturnal monitoring situations in which patient movement is not constantly observed.

Only the inventors have determined the usefulness of impedance values in monitoring and measuring of penile blood flow and other variables, and more specifically, for monitoring and evaluating diurnal or nocturnal erectile events. For the first time, the inventors have developed special apparatus and method features in accordance with this discovery, including features designed to greatly reduce the confusion and potentially false data interpretation associated with artifactual effects.

SUMMARY OF THE INVENTION

To achieve the above-described goals and remedy the above-described disadvantages, a method of monitoring the tumescent state of the penis of a patient includes placing sensing elements in proximity to the penis, sensing penile impedance values with the sensing elements, measuring and/or deriving penile variables such as length values, blood-volume values, cross-sectional area values and/or volume-filling rate values for blood-carrying bodies in the penis using the impedance values, and using the measured and derived penile variables to generate a display output. According to one embodiment, the sensing elements are at least five in number, and include contact electrodes. At least four sensing elements are supported on the penis, two of them in the base region and two in the tip region. The base sensing elements preferably are separate d by a substantially fixed separation distance. One of the tip sensing elements preferably is placed subcoronally. Impedance values can be sensed both in the base region and between the base region and a tip region of the penis, and can be used to derive values such as penile length, blood-volume changes, absolute blood volume, and/or the total cross-sectional area of the blood-encompassing bodies within the penis, according to the invention.

According to another embodiment, an apparatus for monitoring the tumescent state of the penis of a patient includes a plurality of sensing elements to be placed in proximity to the penis for sensing penile impedance values. A processing device is operably coupled, for example by simultaneous or subsequent download link, to the sensing elements and derives penile length and penile blood-volume values using the impedance values. An output device, e.g. a graphical display, outputs the measured and derived penile variables, e.g. for evaluation by the patient and/or a clinician. Artifactual effects easily can be distinguished from erectile events.

According to another embodiment of the invention, an apparatus and/or method of monitoring the tumescent state of the penis of the patient includes determining penile impedance values, determining cardiac-signature data using the impedance values, and using the cardiac-signature data to indicate periods of erectile activity. A pulsatile component of an impedance waveform is determined, and the cardiac-signature data are displayed in graphical form for evaluation of potential organic causes of erectile dysfunction. Both total impedance data and cardiac-signature activity can be displayed simultaneously, the total impedance data optionally being highlighted during certain periods of cardiac-signature activity to reflect potential erectile events.

According to yet another embodiment of the invention, an apparatus for monitoring the tumescent state of the penis according to the invention includes a plurality of spaced contact elements, e.g. electrodes, operably coupled to or near the penis of a patient. The contact elements supply current to penile tissue and permit measurement of a potential difference associated with the combined impedance of blood and penile tissue. Control electronics are operably coupled to the contact elements to determine penile impedance and blood-volume values. At least one of the contact elements is supported on the penis; according to various embodiments up to at least three or four contact elements can be supported on and/or near the penis. At least one electrode can be supported on adjacent anatomical structure of the patient, for example the patient's subumbilical area, leg or groin area close to the penis.

According to embodiments of the invention, blood-volume values can be substantially continuously monitored over time, for example for a length of time sufficient to record a number of erectile events occurring as the patient sleeps. The control electronics preferably are operably couplable with a display apparatus to display substantially continuous impedance, blood-volume, length, and/or cross-sectional area values versus time.

One of the advantages according to the invention is that a housing for the control electronics occupies a significantly reduced space. With surface-mount printed circuit technology, and/or PC card (PCMCIA card) or microcard technology, the housing can be of about credit-card size, or even smaller, and thus easily carried by the patient. According to one example, the housing can be attached to and carried by the patient's leg.

According to another embodiment, a penile tumescence monitoring device includes data storage and/or data processing devices operably coupled to measurement apparatus, which in turn is operatively coupled to the penis. The data storage and/or processing devices are operably coupled to the measurement apparatus for receiving and storing data transmitted therefrom, the transmitted data correlating to e.g. blood volume in the penis. The data processing device determines end output volume values based on the received and stored data. A display device is operably couplable with the data processing device to graph penile blood-volume values over time. A download apparatus is also preferably provided for downloading data from the data storage and/or the data processing device.

According to preferred embodiments, the invention is used for monitoring nocturnal erectile events. According to one embodiment, however, blood-volume values and/or other variables also are monitored and determined diurnally, e.g. for comparison to the nocturnal measurements. Visual observations and ultrasound measurements also can be made diurnally and compared to nocturnal measurements.

Also according to the invention, a method of nocturnally monitoring penile erectile events is provided, the method including the steps of determining nocturnal blood-volume values in the penis, displaying blood-volume data versus time, and using the displayed blood-volume data to diagnose organic and/or psychogenic causes of erectile dysfunction. For example, the displayed blood-volume data can be used to evaluate the relative speed of erection-impairing venous leakage. Further, an erectile event can be medicinally induced while the patient is awake, blood-volume and/or velocity values monitored, and the volume and/or velocity values compared to values determined nocturnally, to evaluate the quality of nocturnal erectile events. Graphical representations of both the nocturnal and diurnal blood-volume values and/or other comparisons allow easy and effective evaluation and comparison.

BRIEF DESCRIPTION OF THE DRAWINGS

Embodiments of the invention will be described with reference to the figures, in which like reference numerals denote like elements and in which:

FIGS. 8–12 are schematic diagrams according to embodiments of the invention;

FIGS. 23–26 are circuit representations according to penile bioimpedance models according to embodiments of the invention;

DETAILED DESCRIPTION OF PREFERRED EMBODIMENTS

1. Introduction

As discussed above, embodiments of the invention have special application to nocturnal monitoring of erectile events, for diagnosing psychogenic and/or organic causes of erectile dysfunction and, in the case of organic causes, for prescribing appropriate therapy, for example, levels of oral medications, levels of transurethral medications, etc. The invention has wide application to a variety of monitoring and testing environments, however. For example, diurnal monitoring is also contemplated, and in many cases a comparison between diurnal and nocturnal measurements can be beneficial in providing an accurate diagnosis. Other embodiments of the invention have application to longer-term testing, for example, for assessment of therapeutic efficacy. Therefore, although preferred embodiments of the invention will be described with respect to nocturnal monitoring and erectile dysfunction diagnosis, the invention is by no means limited to those embodiments.

2. Two-Electrode, Four-Electrode and Other Embodiments

Figure 1:
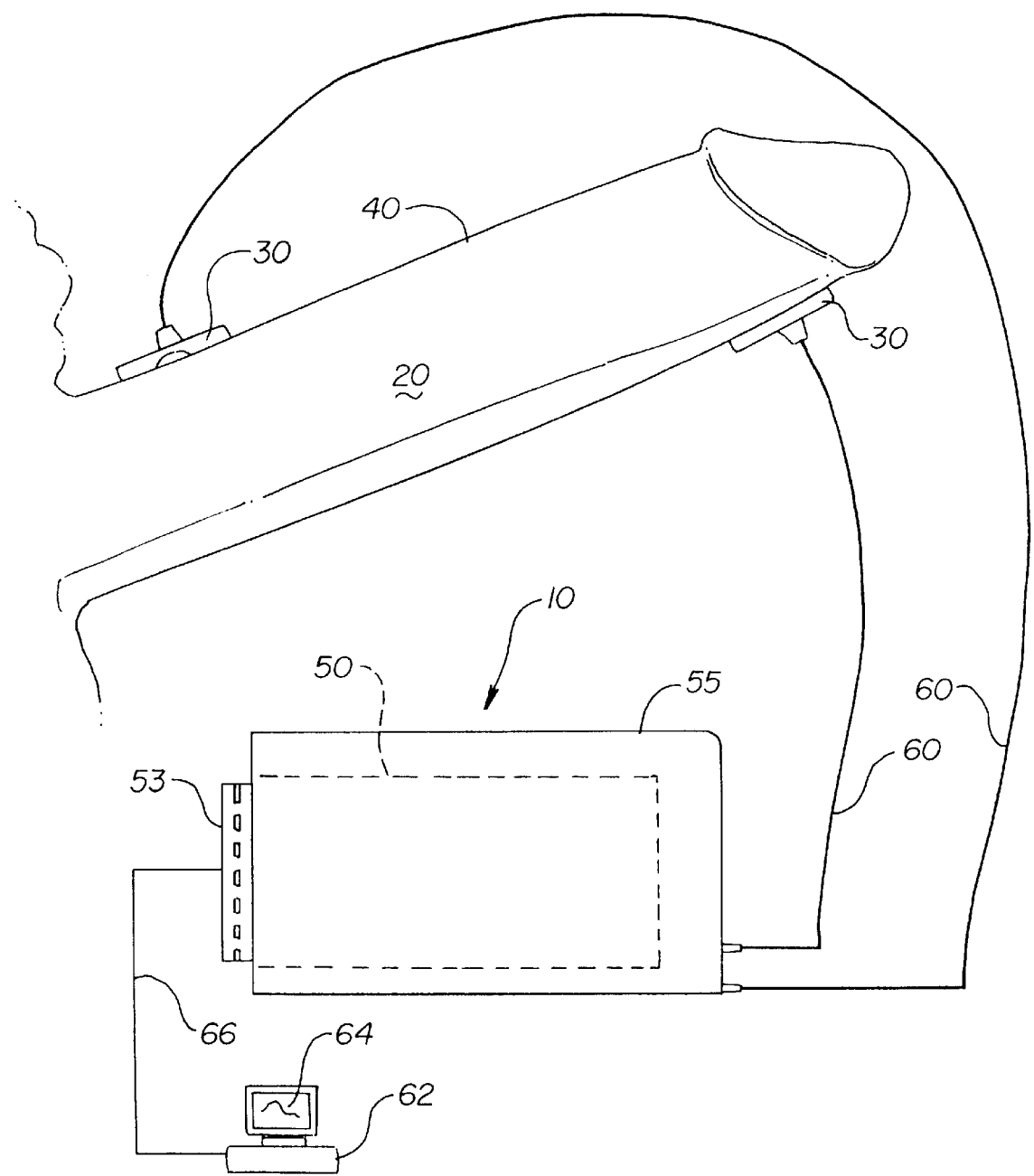
FIG. 1 is a side view of an apparatus embodiment according to the invention.

FIG. 1 shows an erection-monitoring apparatus 10 according to an embodiment of the invention, for monitoring the tumescence/rigidity of penis 20 of a patient. Erection-monitoring apparatus 10, also called a penile tumescence monitoring device, preferably includes a plurality of spaced contact or measurement elements 30 operably coupled to penis 20, for example by direct contact through a gel or other conductive layer. According to the FIG. 1 embodiment, contact or sensing elements 30 include two spot electrodes, one placed at the base and one placed near the tip of penis 20, on opposite sides. A preferably constant, sinusoidal alternating current passes longitudinally through penis 20 between the electrodes, and the potential drop across the electrodes is measured. According to one embodiment, an alternating current with a frequency of about 100 kHz is used, although frequencies of about 5 kHz to about 2 MHz are also contemplated, and even frequencies beyond these ranges, or direct currents, can be used as well.

Two-electrode embodiments according to the invention work well for certain applications. A problem arises, however, in that the impedance of each contact element itself can be quite high relative to the changes in impedance that are measured and evaluated. Further, pressure-induced variations in the contact impedance due to random patient movement can obscure the impedance changes due to the erectile event. Therefore, FIG. 2 shows an embodiment of the invention in which contact elements 30 comprise four circumferential or partial circumferential electrodes, extending substantially entirely around penis 20.

Partial circumferential electrodes according to one embodiment of the invention include silver ink traces printed on TYVEK or other material, which is placed on foam tape. The tape then is wrapped around the penis for secure and comfortable contact.

Figure 2:
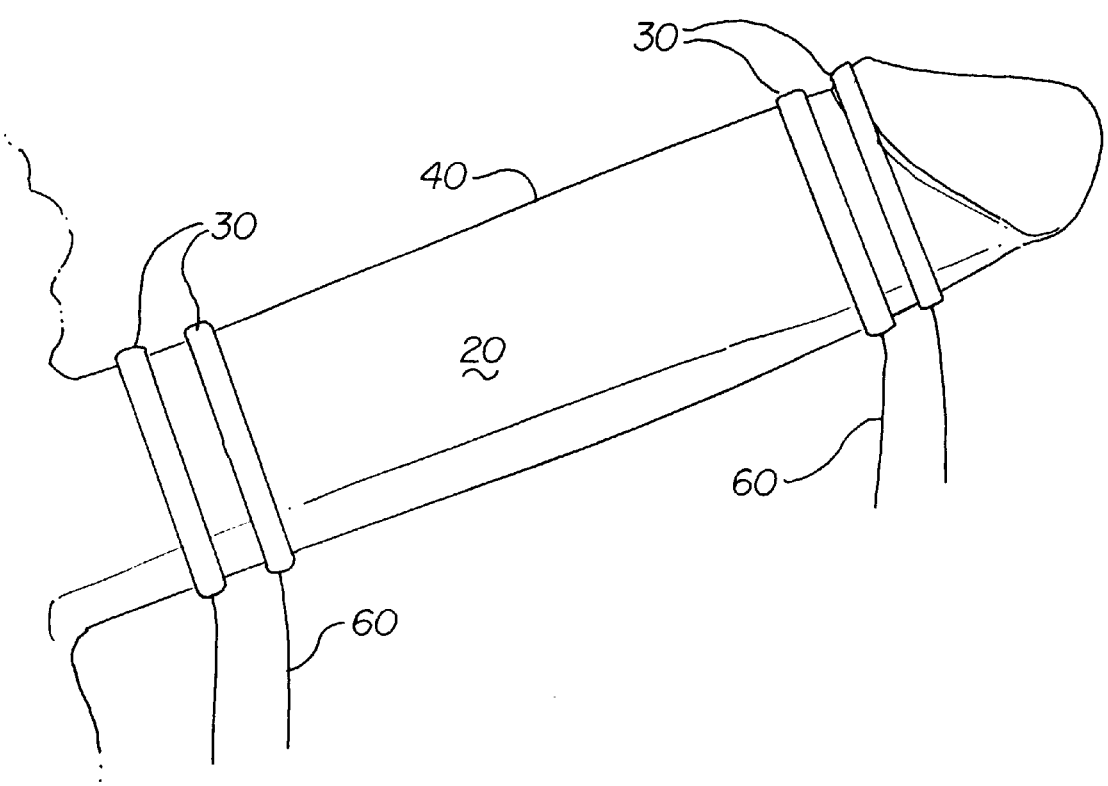
FIG. 2 is a side view of an apparatus embodiment according to the invention.

According to the FIG. 2 embodiment, the two outer electrodes 30 supply the current passing longitudinally through penis 20, and potential voltage drop is determined across the two inner electrodes 30. Because a constant current source is used to supply current to the two outer electrodes, the impedance of these electrodes does not affect the amplitude of the applied current. Also, because an amplifier having an input impedance much higher than the inner electrodes is used to monitor the electrode voltages, the impedance or change in impedance of the electrodes does not effect the voltage measured. Therefore, the four-electrode embodiment avoids the electrode impedance sensitivity problem of the two-electrode structure.

Of course, two circumferential or four spot electrodes are also among the contact element embodiments contemplated according to the invention. Three-electrode embodiments are also contemplated, for example with electrodes placed at the tip of the penis, i.e. at the glans penis or subcoronally, at the base of the penis, and subumbilically or at the groin. The outer electrodes supply current, and potential voltage drop is measured preferably between the base and the tip electrodes. Tip, groin and subumbilical electrode placement are also possible.

According to one embodiment, a conductive adhesive can be used to conductively connect electrodes 30 to tissue 40 of penis 20, to enhance conductivity and to substantially reduce the likelihood of artifactual effects caused by e.g. excessive movement of the penile tissue or poor electrode connection. Conductive adhesive suitable for use according to the invention is available from 3 M, St. Paul, Minn. or from LecTec Corporation, Minnetonka, Minn., for example. Preferred conductive adhesives will be elastic enough to accommodate enlargement of the penis during an erectile event, and may be combined with distensible cloth or an elastic band. Further, a flexible copper tape or similar conductive material can be wrapped around the conductive adhesive to ensure a strong, stable electrical connection and thereby reduce artifactual effects.

According to one embodiment, the electrodes are partial circumferential electrodes extending between about one-half and about one-third around the penis. Foam tape securing each electrode in place extends about halfway around the penis. This arrangement substantially avoids constriction, thereby leaving movement/enlargement of the penis substantially unaffected and minimizing patient discomfort.

3. Control Electronics

Operably coupled with the contact elements of any of the embodiments described in this application are control electronics 50 (FIG. 1), which can include data processing and storage devices and which are used e.g. to determine tissue impedance values between at least two of contact elements 30 and to determine penile blood-volume values, and/or volume-change values, based on the impedance values. (For purposes of this application, the terms volume values and volume-change values may be used interchangeably as needed). Examples of control electronics 50 and/or other electronics suitable for use according to the invention are shown in the block diagram and schematics of FIGS. 7–12, and can include, for example, an A/D converter, microcontroller and random access memory (RAM). Control electronics 50 are connected to contact elements 30 via plug-in wiring 60 or other suitable data-transmission device(s).

Control electronics 50 are preferably disposed within a modular box or other housing 55, according to one embodiment. Connector 53 is e.g. a sub D connector to be used for connecting control electronics 50 with data processing device 62 and/or display device 64 through a cable for either simultaneous or subsequent data download. Other data transmission device(s) 66, e.g. fiber optic cable or a wireless link can also be used. According to one embodiment, at least portions of control electronics 50 can be included in a PC card and/or associated circuitry, a microcard, or similar substantially modular, readily interchangeable computing technologies.

Given the small sizes associated with these technologies, housing 55 for control electronics 50 can be of greatly reduced size, for example, credit-card size or even smaller. According to one embodiment, housing 55 has a volume of less than about 60 cc, and a maximum thickness of less than about 12 mm.

The impedance from the current flowing through the penile blood and tissue generates a potential voltage difference between the two inner electrodes 30. Data representing this voltage difference and/or the associated impedance is transmitted to control electronics 50 for processing and storage by the data processing and storage devices included within or associated with control electronics 50. As will be described, blood-volume changes are important to an accurate diagnosis.

Certain embodiments according to the invention, e.g. three-electrode embodiments, can be used to measure stroke volume over time, i.e. the bolus of blood delivered during each cardiac cycle. Summing these bolus values yields the total volume increase of blood in the penis during the erectile event.

It should also be noted that a considerable amount of research has been conducted relating to the conductive properties of various biological tissues. See, for example, Geddes, L. A., et al., "The Specific Resistance of Biological Materials—A Compendium of Data for the Biomedical Engineer and Physiologist," *Medical and Biological Engineering*, Vol. 5, 1967, pp. 271–293. The resistivity values presented in the Geddes article may have value in considering the theory behind embodiments of the present invention.

The theory behind certain embodiments of the present invention considers that as the penis changes from flaccid to erect, the increase/decrease in the volume of the penis (circumference and length) is due to greater/lesser volume of blood, while the tissue volume remains constant. The measured impedance increases as the penis becomes longer, and decreases as the penis again becomes flaccid.

4. Off-Penis Electrodes

Figure 3:
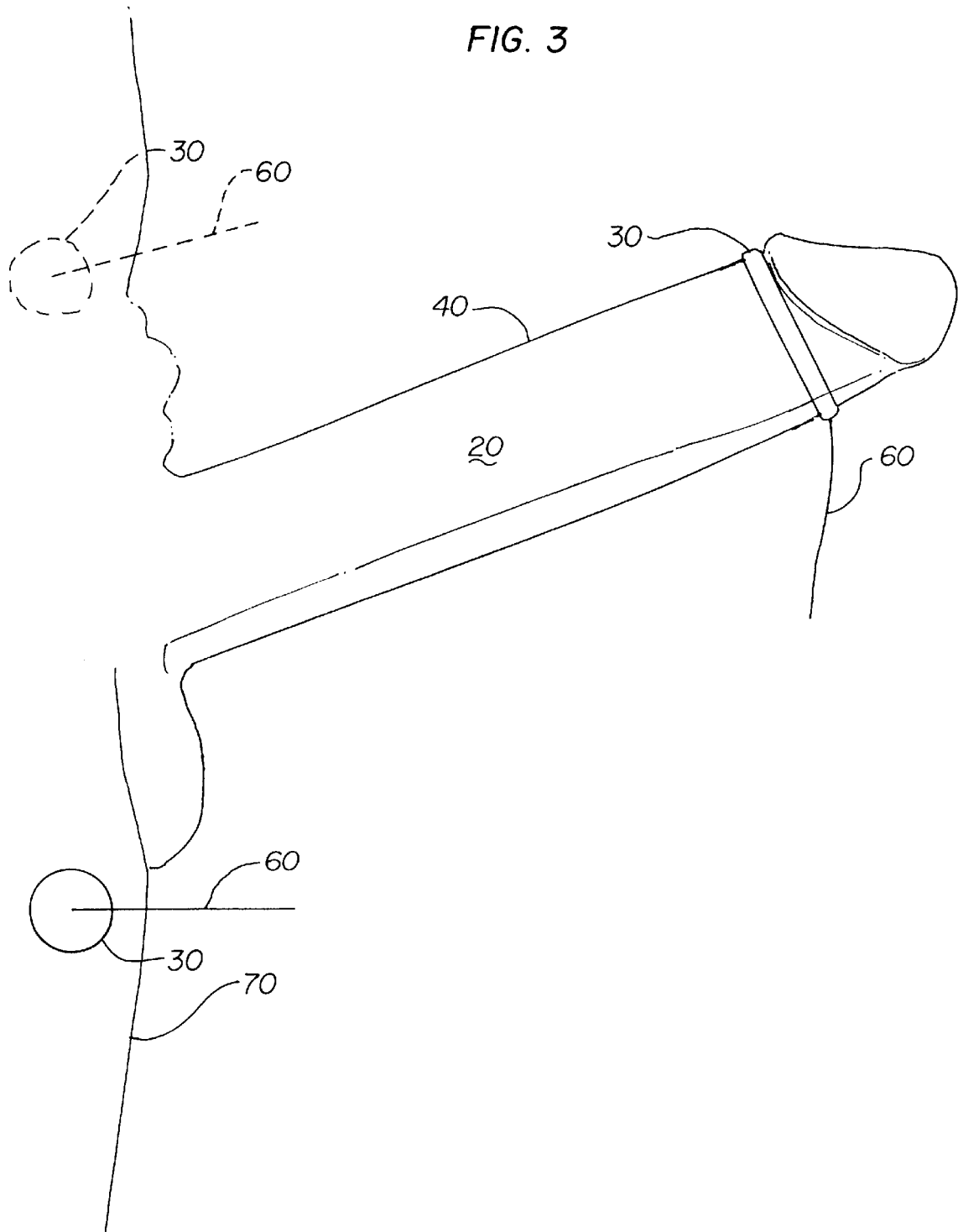
FIG. 3 is a side view of apparatus embodiments according to the invention.

According to the FIG. 3 embodiments, one electrode 30, for example, a circumferential or partial circumferential ring electrode, is secured to the tip of the penis, more specifically the glans penis, or subcoronally. A second electrode 30 is mounted on the hip or groin area of the patient's leg 70 or, as shown in dashed lines, subumbilically, preferably on the midline of the patient. The only area changing significantly in volume between the electrodes is the penis, so the basic theory behind the invention remains valid.

The FIG. 3 embodiments are especially advantageous, because although inter-electrode distance is increased slightly, artifactual effects associated with the electrodes are significantly decreased. Artifactual effect considerations with penile impedance measurements are not insignificant, because the skin of the penis is generally loose and moveable, and the penis of course changes length, circumference and volume during an erectile event. Bodily movement of e.g. the torso and/or the penis itself can also cause artifactual effects, as will be described. Placing one electrode 30 off penis 20 as shown, instead of on the base of the penis, enhances contact stability and minimizes certain types of artifactual effects. Additionally, subumbilical or hip/groin placement is generally more comfortable for the patient because the pubic hair in the area of the base of the penis is not affected. Subumbilical or hip placement is also believed to reduce the likelihood of electrode dislodgement when the patient rolls over or otherwise moves during sleep.

5. Data Display

Figure 4:
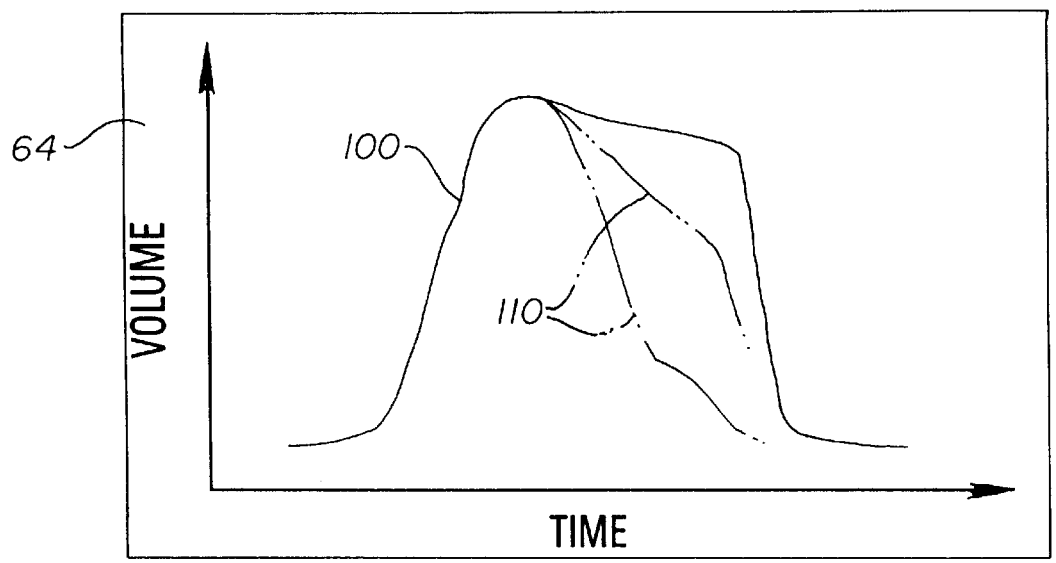
FIGS. 4–6 are sample blood-volume graphs according to embodiments of the invention.
Figure 5:
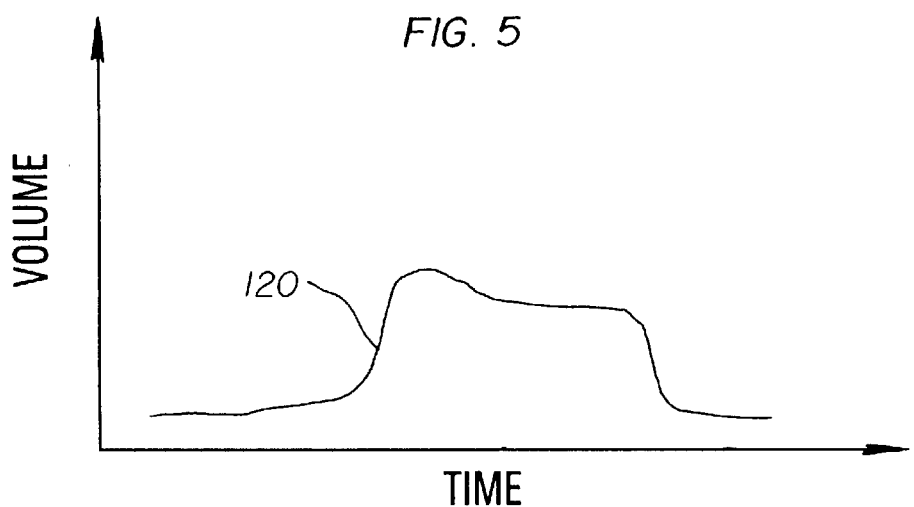
Figure 6:
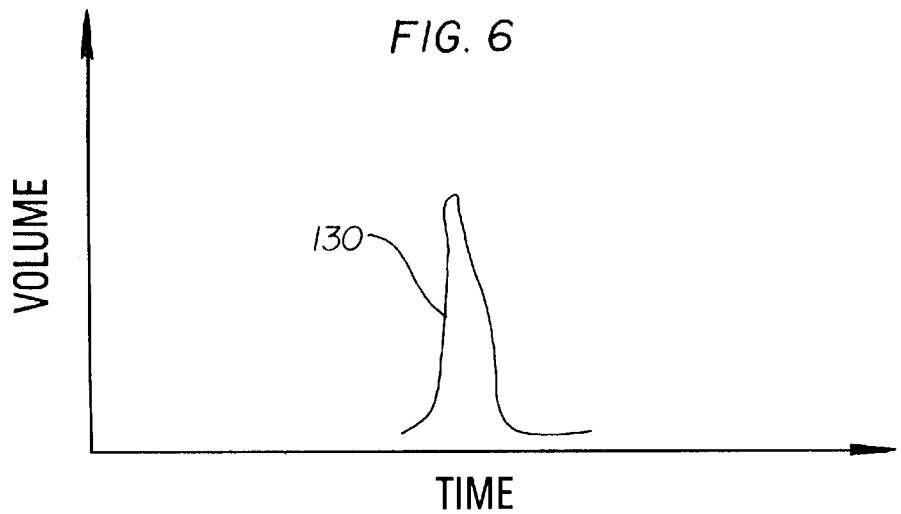
Figure 7:
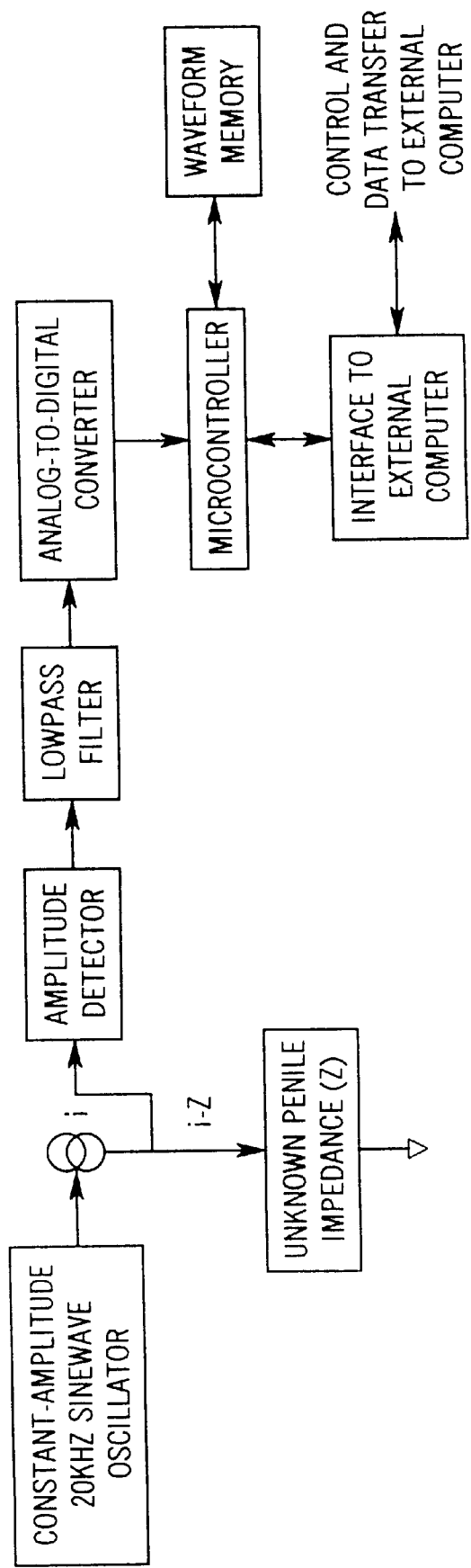
FIG. 7 is a block diagram according to an embodiment of the invention.
Figure 9:
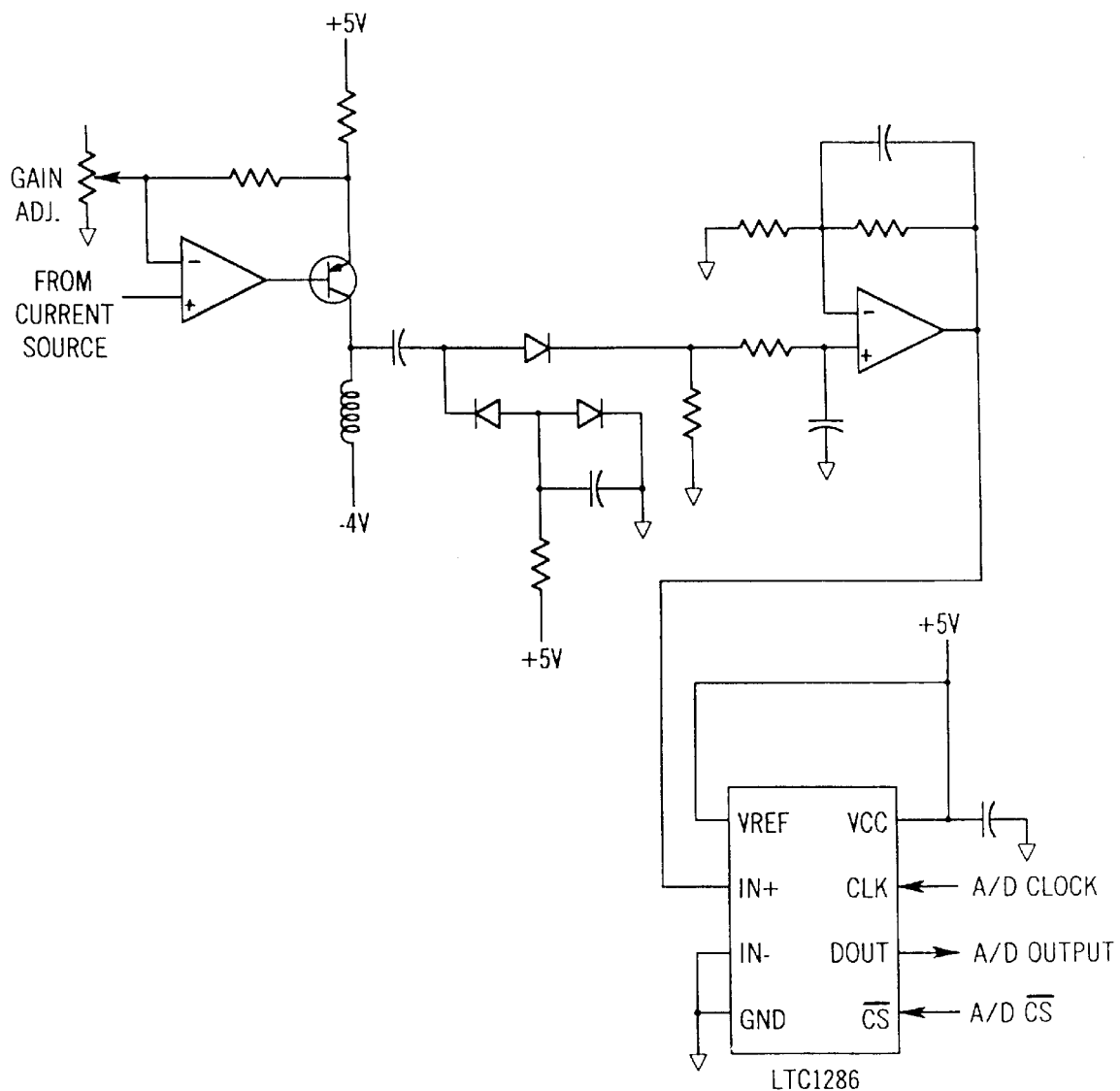
Figure 10:
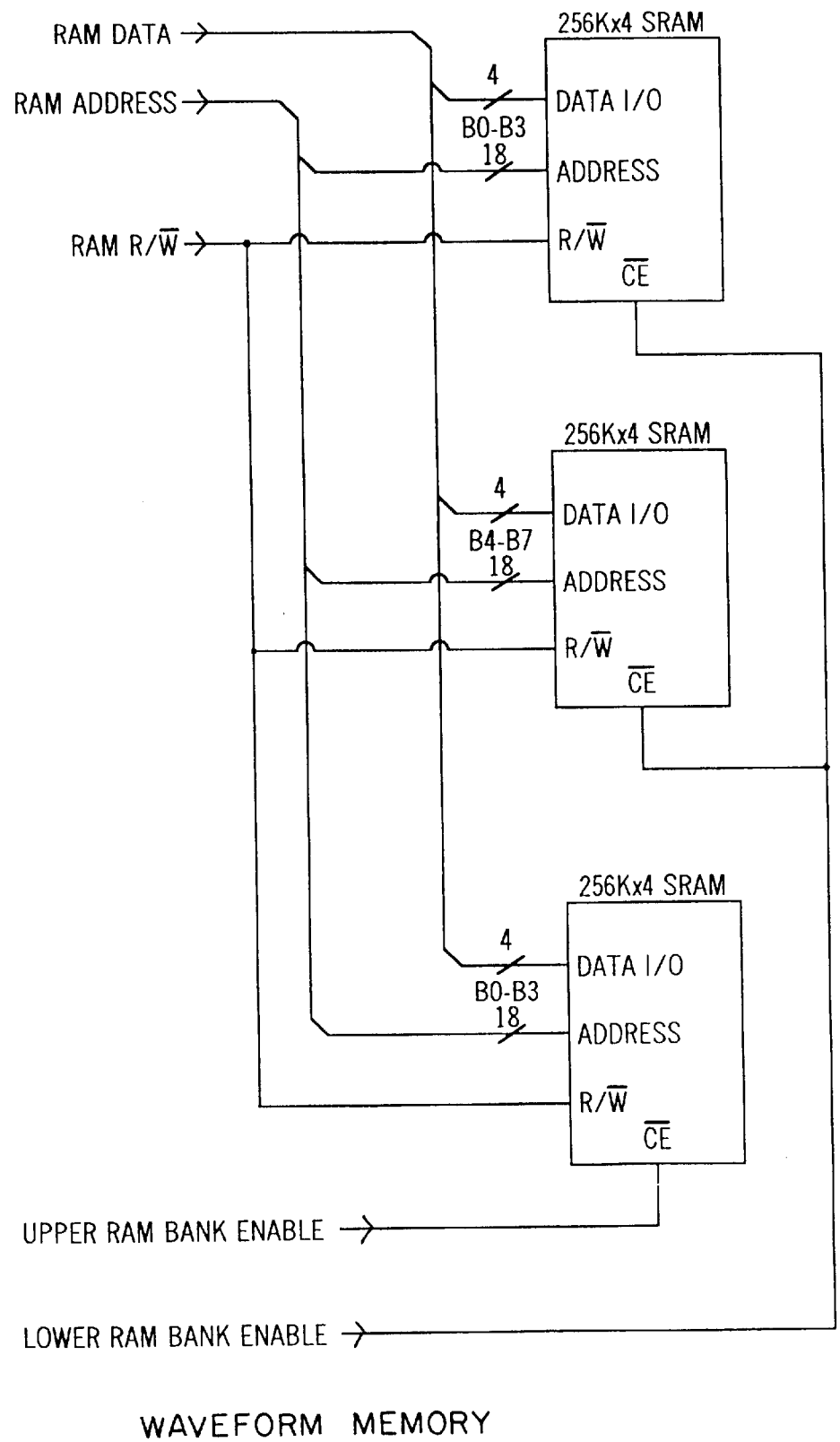
Figure 11:
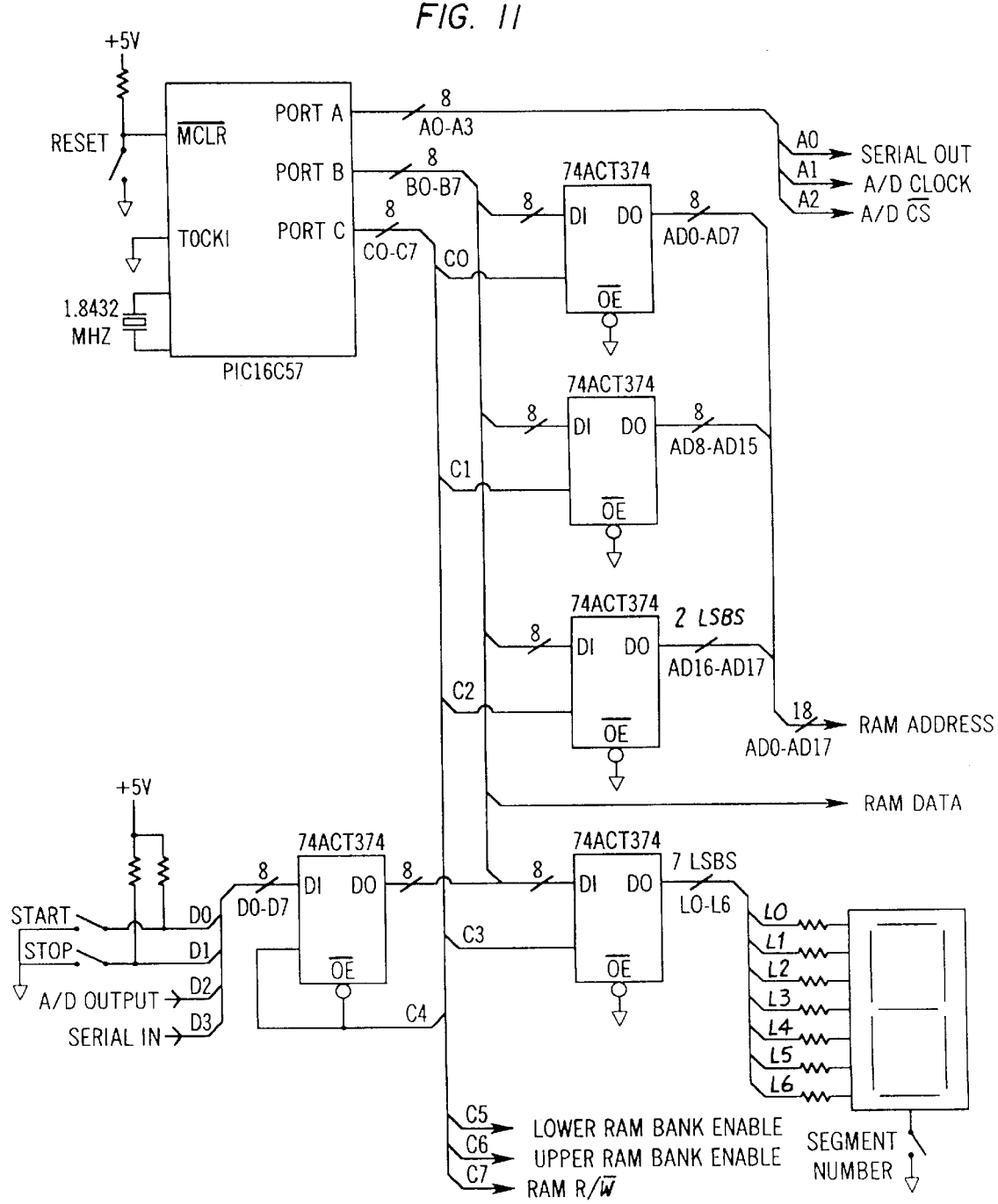
Figure 12:
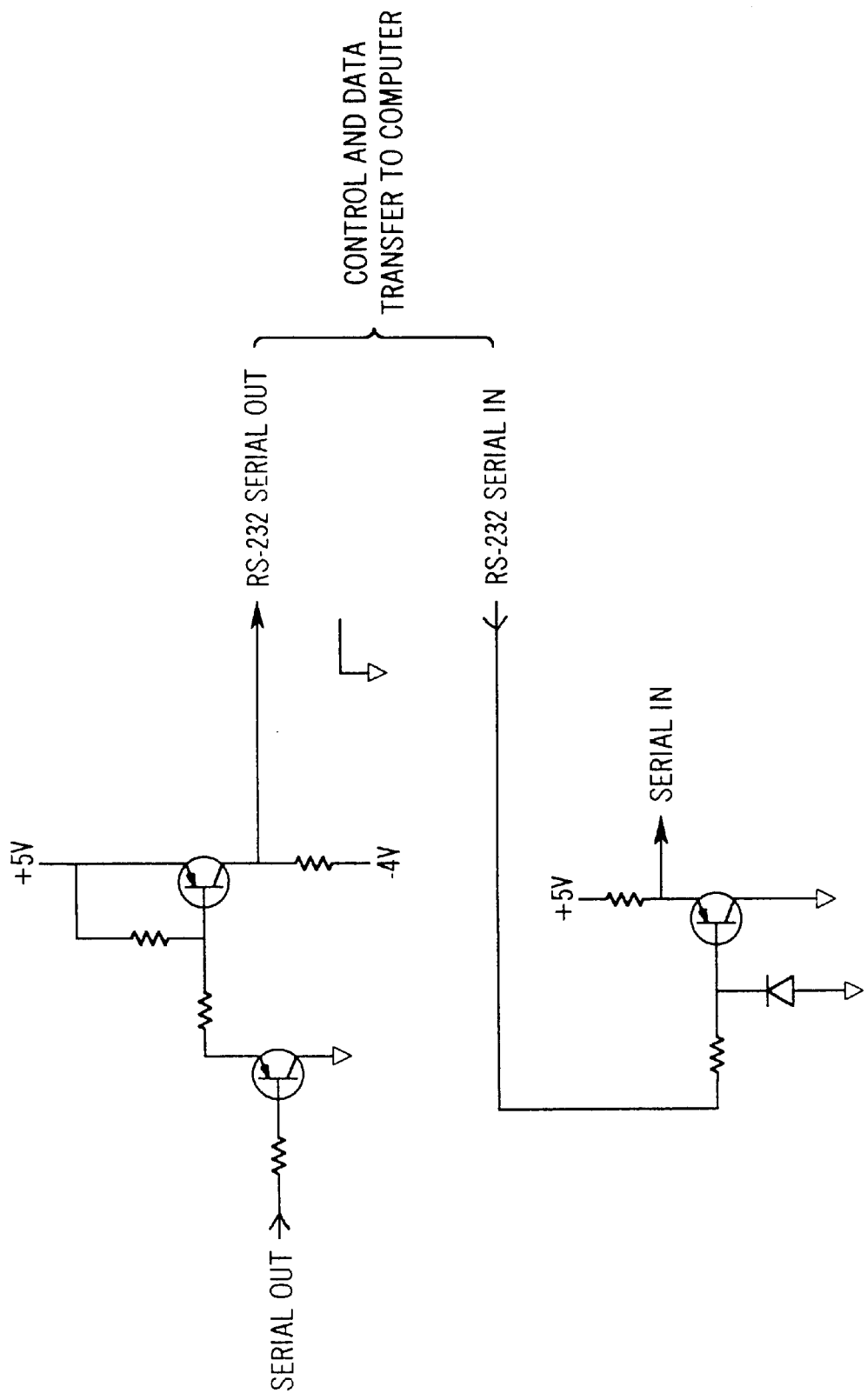

According to one embodiment, data processing device and/or display devices 62, 64 are operably couplable via e.g. a download link to the data-processing and/or—storage devices associated with control electronics 50, to graph or otherwise display penile blood-volume values over time. Examples of such graphs are shown in FIGS. 4–6. These graphs allow the medical professional to more readily evaluate and diagnose erectile dysfunction based on relative changes in blood volume, and not necessarily absolute blood-volume measurements themselves.

Curve 100 of the volume versus time graph illustrated on display 64 in FIG. 4, for example, is believed to reflect a normal erectile event. A series of normal erectile events throughout the night would tend to indicate that any diurnal erectile dysfunction is likely psychogenic in origin. Curves 110 demonstrate that these normal events may vary in duration throughout the nocturnal measurement period. Curve 120 of FIG. 5 would tend to indicate low penile blood volume, perhaps associated with impaired arterial mechanisms. Finally, curve 130 of FIG. 6 would reflect an extremely fast venous leakage.

Software associated with control electronics 50 and/or display 80 can detect erectile events such as those indicated by curves 100–130 over the many hours of data potentially recorded. By honing in on those portions of the data that are of interest, and by displaying the corresponding blood-volume data graphically, the medical professional is more easily able to make an accurate diagnosis.

6. Diagnostic Protocols

To further enhance evaluation and diagnosis, according to one method of use, a patient experiencing erectile dysfunction meets with a medical professional at the medical professional's office. Impedance/volume measurements are made with the penis in the flaccid state, and blood-velocity measurements are optionally made as well. An erection is then induced medicinally, e.g. by injection, transurethral administration, or oral administration of an appropriate drug. As the erection progresses, measurements of impedance change over time are taken, resulting in blood-volume and other variable derivations and measurements that can be used in corresponding graphical displays. By visually observing and recording the quality of the erection, e.g. by physically observing or measuring circumference and/or length or even taking ultrasound measurements, and then associating these observations with the corresponding volume and/or velocity data, the medical professional gains valuable, customized knowledge for later reference and comparison to nocturnal data.

The patient then returns home, preferably with electrodes or other contact elements in place as applied or demonstrated by the medical professional. This reduces the likelihood of patient error in placing the electrodes at home, although of course patient-placement is possible according to the invention. The small size of housing 55 and associated electronics 50 allow the overall device to be worn home easily. Housing 55 can be strapped to the patient's leg with VELCRO straps, for example, or otherwise mounted on or carried by the body.

Following the night's measurements, the patient can remove the electrodes and return the device to the medical professional's office. If data readings for additional nights are desired, the patient can either reapply the electrodes himself in the evening before sleeping, or return to the doctor's office to ensure proper electrode placement for the second and any subsequent nights. Additionally, the patient can download data from home to the medical professional's office by e.g. telephone or online link. The medical professional can then evaluate the data and determine whether monitoring over additional nights will be necessary. The monitoring device conveniently may be equipped with an on/off switch or mechanism, to conserve power when monitoring is not occurring.

After nocturnal measurements are made over one or more nights, as needed, data from the data storage and/or processing devices is downloaded to a separate device, for example a personal computer with display 80, for further processing and/or display. Visual comparisons can be made between volume-versus-time graphs for nocturnal erectile events and the erectile event(s) medicinally induced in the medical professional's office, if any. The graphs of the events can be displayed side-by-side on the same display screen, for example, to facilitate the comparison.

7. The Problem of Artifactual Effects

Figure 13:
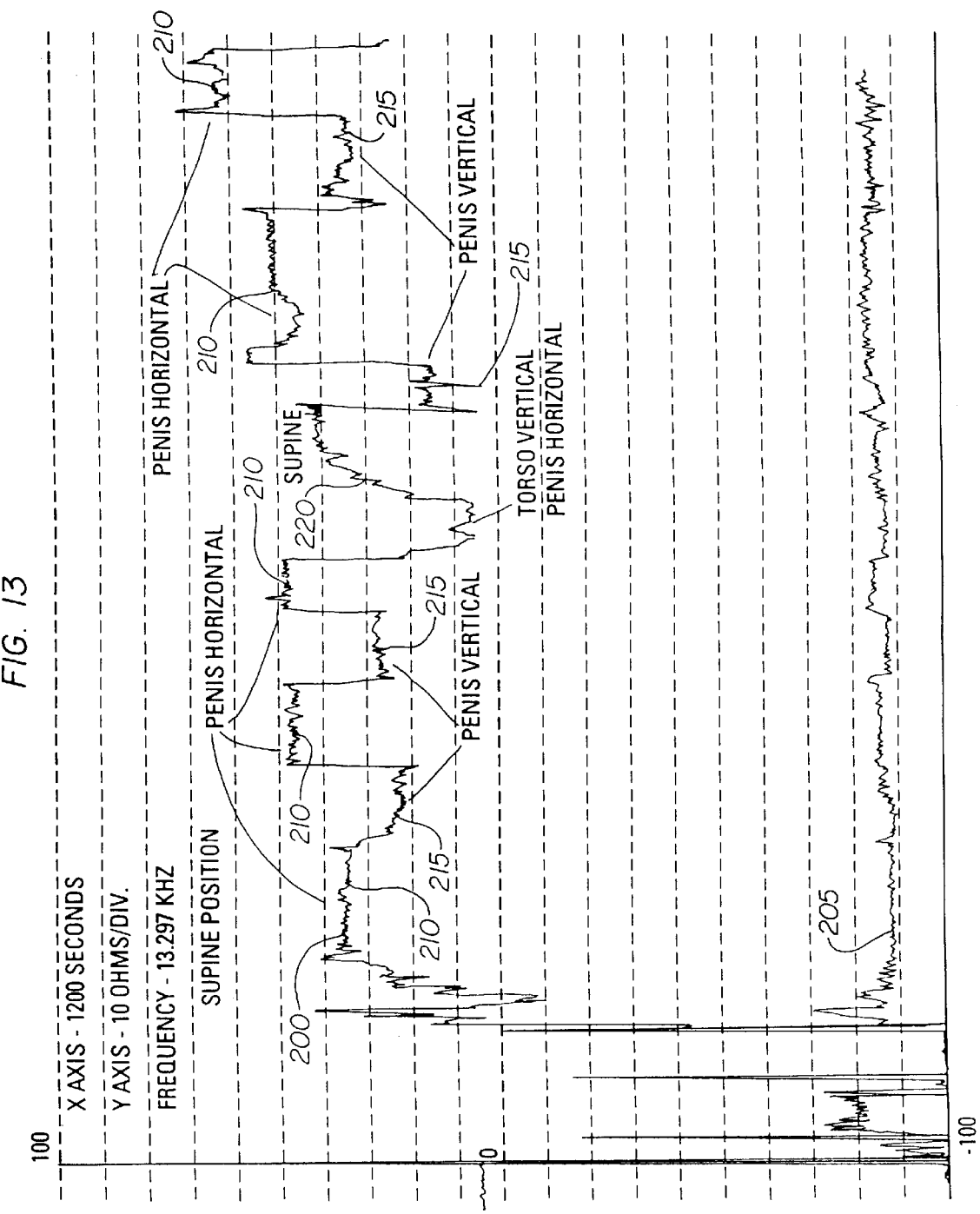
FIG. 13 is a graph of impedance values showing movement-induced artifacts, according to an embodiment of the invention.
Figure 14:
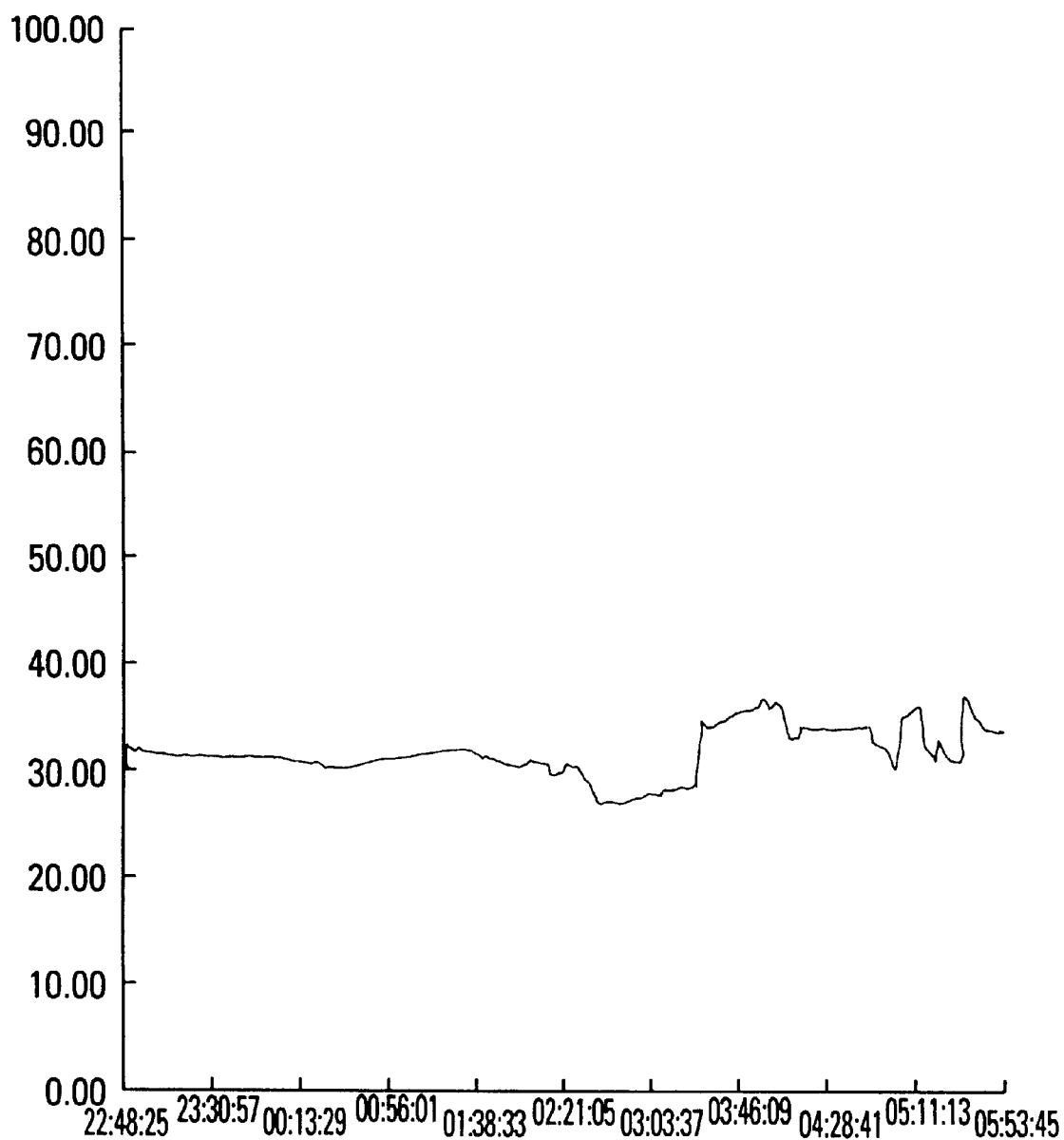
FIGS. 14–19 are further impedance plots according to embodiments of the invention.
Figure 15:
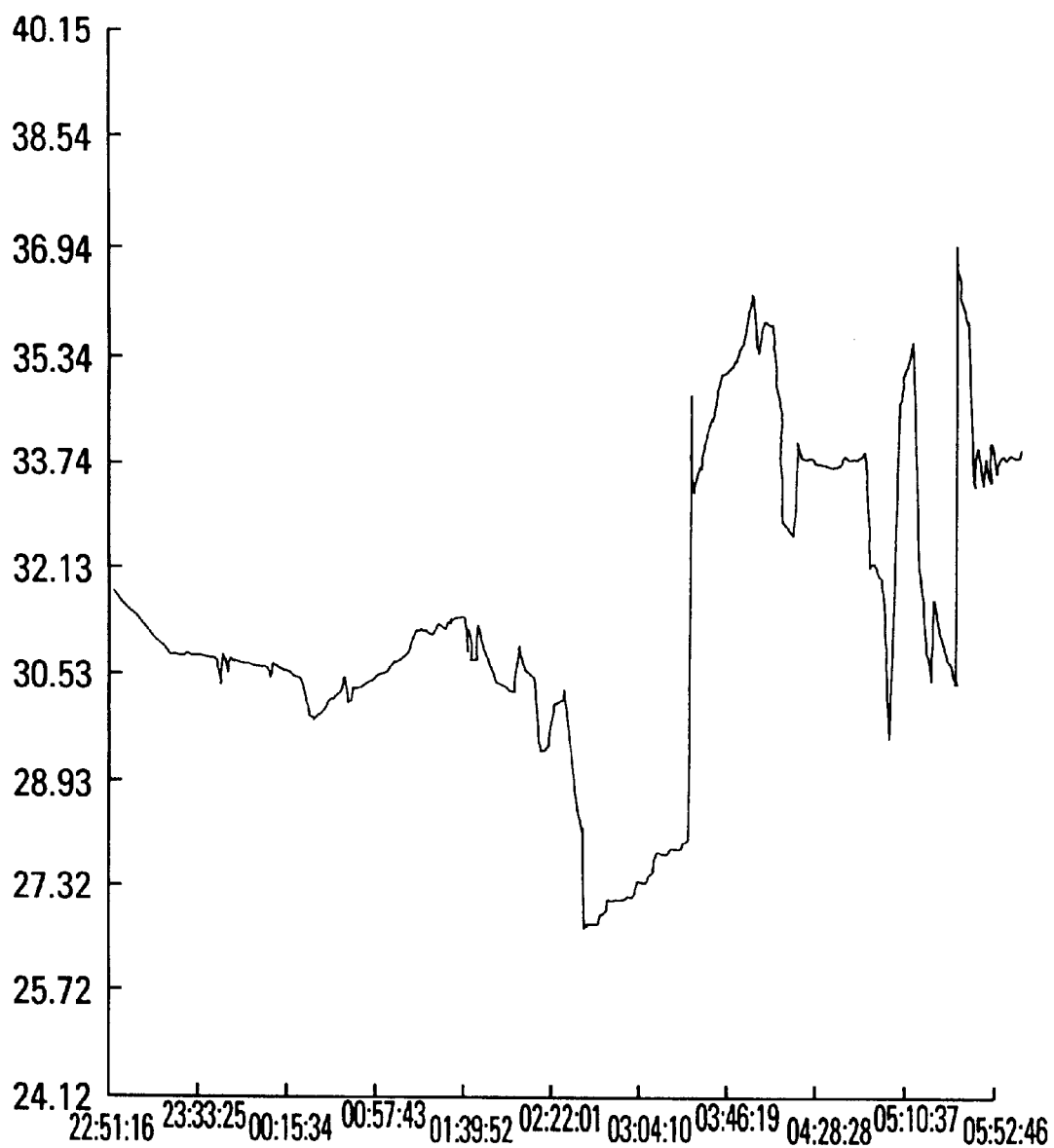
Figure 16:
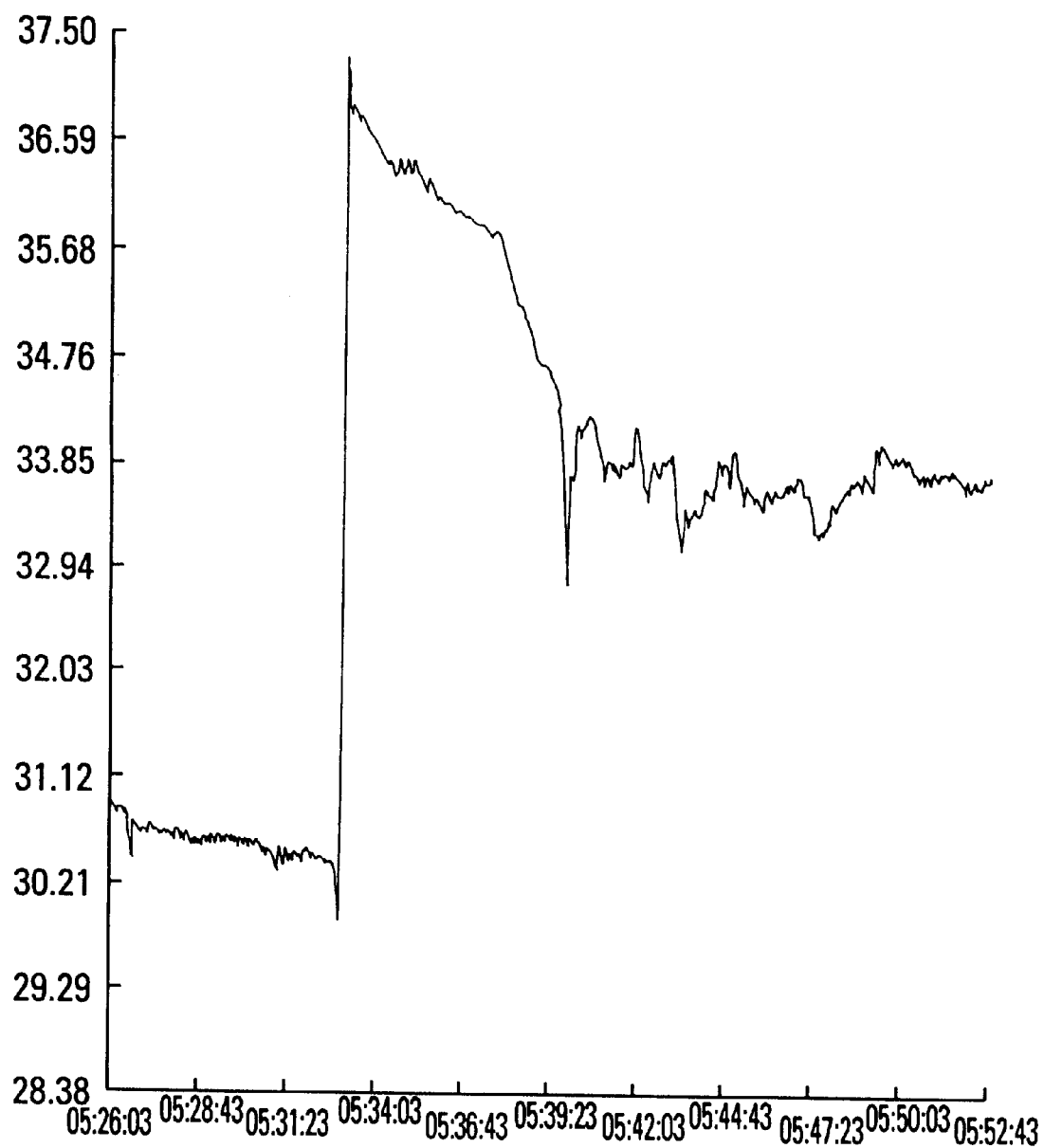
Figure 17:
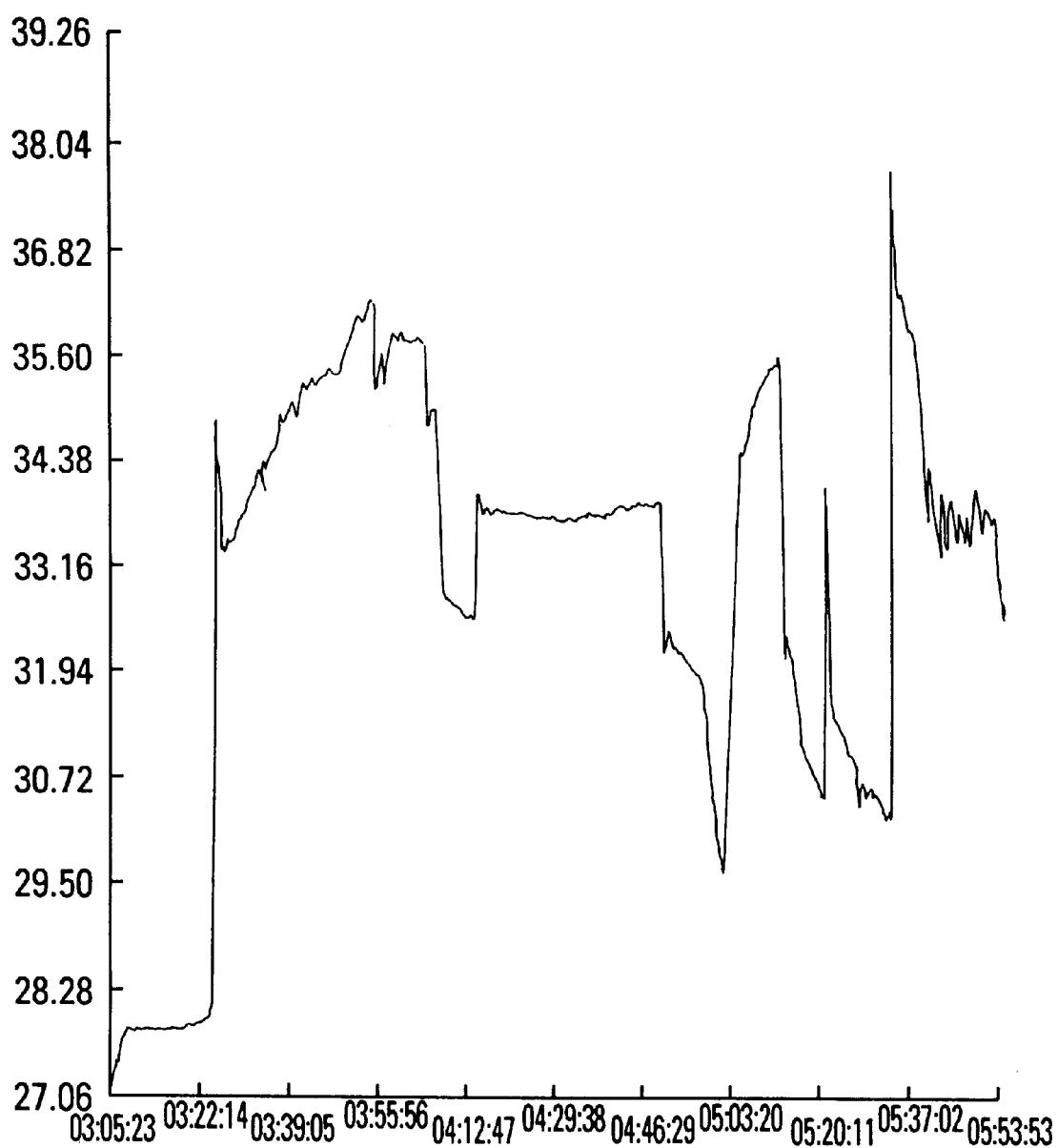
Figure 18:
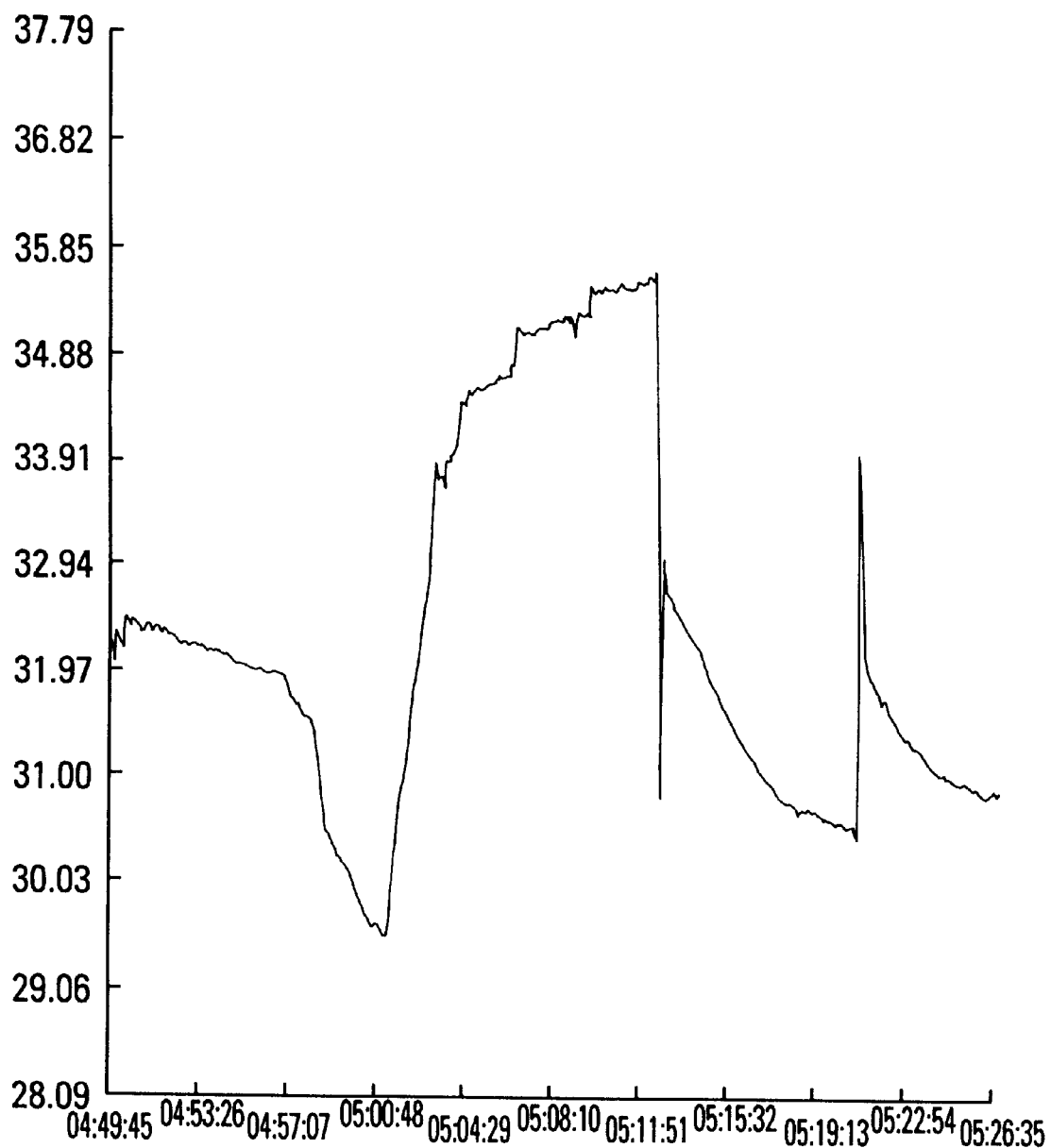
Figure 19:
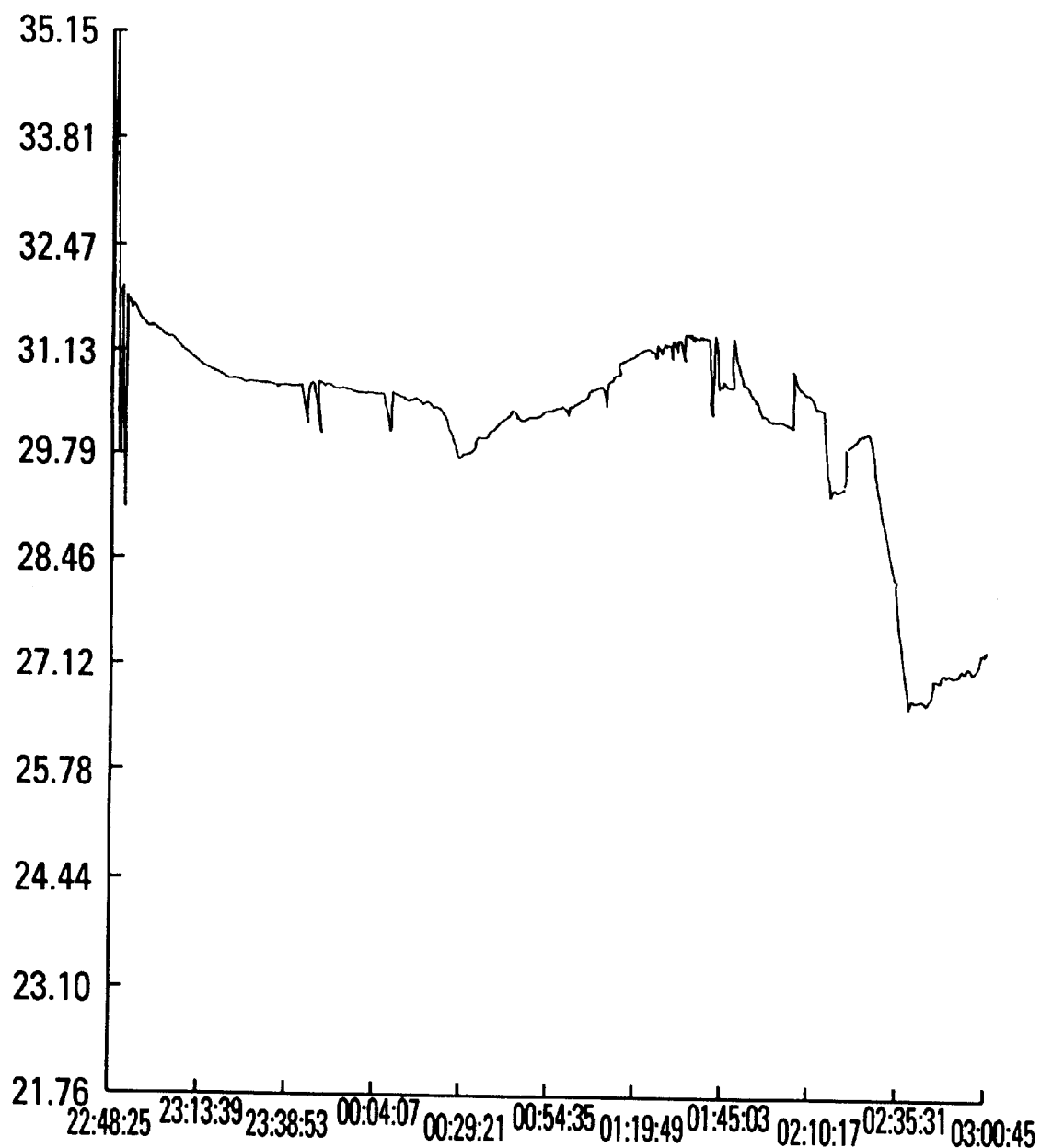

As referenced above, artifactual effects can complicate the interpretation of impedance data produced by embodiments of the invention in certain situations. FIG. 13, for example, shows a graph of measured penile impedance versus time over a period of approximately 20 minutes. Curves 200, 205 represent the real and imaginary components of impedance, respectively. As shown, curve 200 varies significantly as the position of the penis shifts back and forth from horizontal to vertical; note, for example, penis-horizontal portions 210 of curve 200, and penis-vertical portions 215 of curve 200.

Additionally, impedance curve 200 varies significantly with torso movement. Portion 220 of curve 200, for example, reflects a shift in torso position from vertical to supine, as indicated. Given the multiple shifts in torso and penis positions that can occur throughout a period of nocturnal monitoring, and given the lack of direct observation of such movements, evaluating a graph such as that of FIG. 13 can be problematic.

FIGS. 14–19 are graphs showing variation, over one night's testing, of impedance with time, impedance being shown as a percentage of a 500-ohm maximum impedance obtained using a two-electrode embodiment. Different figures use several different scales in the X and Y axes. As is evident, these graphs contain substantial amounts of data and can be the subject of rigorous analysis to determine the various impedance mechanisms associated with erectile and non-erectile events. Interpreting the graphs without training or background information, however, can be difficult. Additionally, artifactual effects complicate the interpretive process.

8. Five-Electrode Embodiments

According to a primary embodiment for overcoming the interpretive difficulties associated with artifactual effects, five sensing elements are used to make two different penile impedance measurements throughout the monitoring period. Penile variables, such as penile length, absolute blood volume, blood-volume change, volume-filling rate, and/or cross-sectional area values, are then measured or derived according to a bioimpedance model of the penis, as will be described, and can be displayed for easy interpretation by the clinician or even by the patient himself. According to embodiments of the invention, the term "blood-volume" values as used throughout this application can be interpreted as values reflecting absolute blood volume, or reflecting change in penile blood volume, as described earlier. "Cross-sectional area" values should be interpreted throughout this application as values reflecting the cross-sectional area of one or more blood-carrying bodies in the penis.

Figure 20:
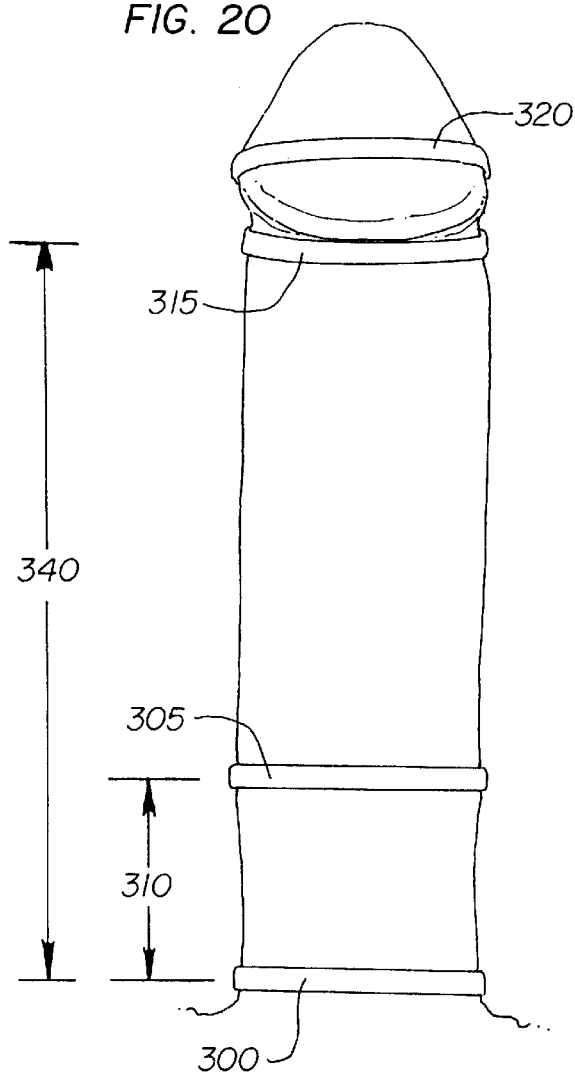
FIGS. 20–21 show an embodiment of the invention using five contact elements.
Figure 21:
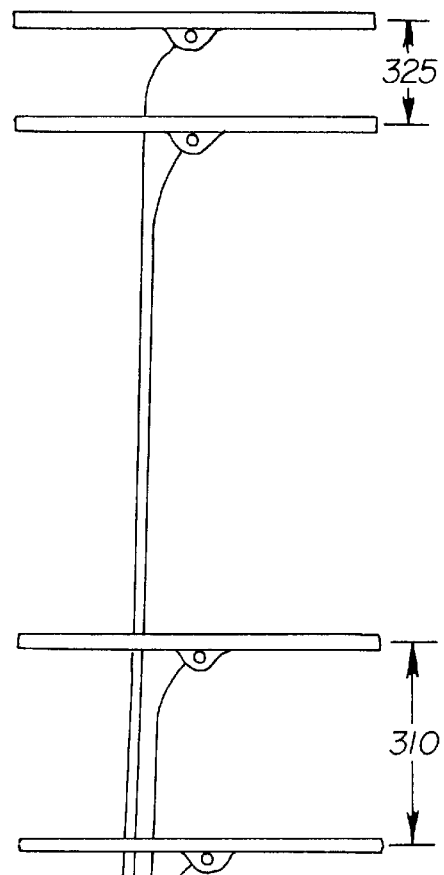
Figure 22:
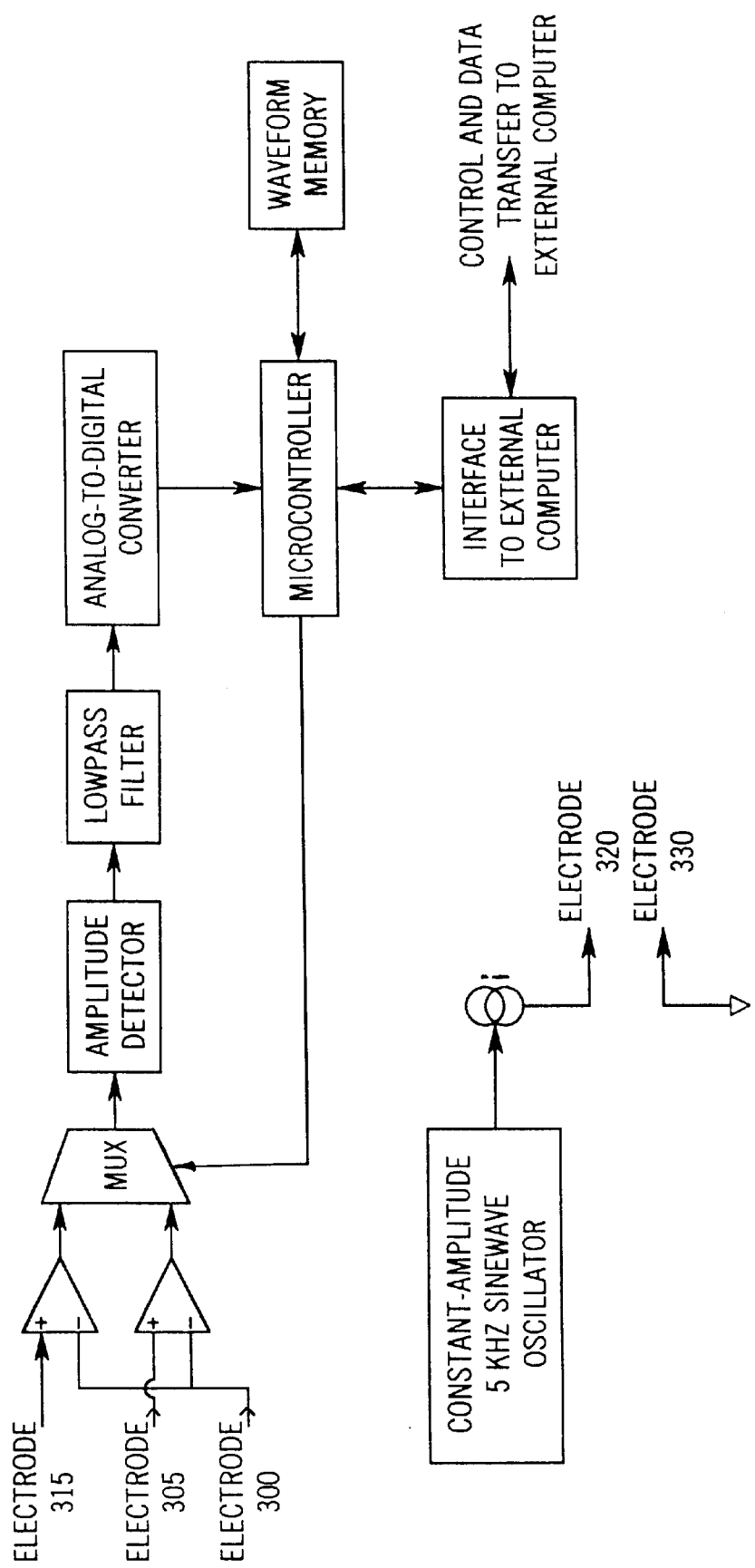
FIG. 22 is a block diagram according to an embodiment of the invention.

As shown in FIGS. 20–21, two contact elements 300, 305, i.e. first and second base electrodes, are placed on the base of the penis and are spaced by a substantially fixed distance 310, for example about 2 cm. At the distal end of the penis, contact element 315 is placed e.g. subcoronally and contact element 320 is placed e.g. on the glans. These subcoronal and distal electrodes 315, 320 are separated by a substantially fixed distance 325, e.g. about 1 cm. Fifth contact element 330 is placed on the hip, subumbilically, or in another desired position on the body of the patient, preferably off the penis. Leads 335 connect each of the contact elements with a suitable connector (not shown) for data transfer to another location, by e.g. simultaneous or subsequent download link. According to one embodiment, leads 335 can be attached to a snap-in phone-plug-type connector. Connectors and associated circuitry and control electronics similar to that described with respect to earlier embodiments can be used, of course. FIG. 22 is a block diagram showing one embodiment of control electronics 50 for a 5-electrode embodiment of the invention.

Contact elements 300, 305, 315, 320 and 330 preferably are relatively thin, circumferential-wrap or partial circumferential-wrap electrodes, such that separation distances 310, 325 are relatively large compared to electrode thickness. Contact-element pairs 300, 305 and 315, 320 can each be secured to a piece of tape, adhesive bandage, or similar material to substantially fix separation distances 310, 325 even during an erectile event. Each penile contact element preferably includes a circumferential gap, to avoid constricting the penis as it enlarges. According to one embodiment, the electrodes are partial circumferential electrodes extending between about one-half and about one-third around the penis. Foam tape securing each electrode in place extends about halfway around the penis. This arrangement substantially avoids constriction, thereby leaving movement/enlargement of the penis substantially unaffected and minimizing patient discomfort.

In operation, distal electrode 320 injects current into the penis, and off-penis electrode 330 provides a current-return path. By measuring voltage drop and/or impedance between first base electrode 300 and subcoronal electrode 315, and between first base electrode 300 and second base electrode 305, enough information can be obtained to substantially determine/estimate parameters such as length 340 between electrodes 300, 315 and change in penile blood volume over time. Length 340 can be considered an effective length of the penis for purposes of discussion.

According to preferred embodiments, the injected current is at a low enough frequency, e.g. about 1–20 kHz, that the imaginary parts of the measured complex impedance values are negligible. The measured impedance magnitude, therefore, corresponds to the real part of the actual impedance, which is the inverse of admittance. Higher frequency values, e.g. in the 100 kHz range, likely would require a somewhat different circuit and analysis than described herein, but of course such current values are still within the spirit and scope of the invention.

More detailed derivation models according to embodiments of the invention will now be described.

9. Derivation Model I a. Penile model

For the purpose of deriving a bioimpedance model of the penis, presume that the penis can be decomposed into two regions filled with homogeneous (in terms of resistivity) material that are, from a circuital standpoint, in parallel. FIG. 23 shows the length, cross-sectional area, and resistivity of the two regions. The regions denoted by the subscripts b and t are the blood- and tissue-filled volumes.

The admittance of each region is similarly denoted by $Y_b$ and $Y_t$. These admittances are measured by thin electrodes that encompass the areas at the ends of the segment, however there is a gap in the electrodes so as not to constrict the area from enlarging. An AC current of constant magnitude flows through the total region, and the admittance is measured as the (complex) ratio of this source current to the voltage measured between the electrodes. Also, this current is applied by electrodes at a sufficient distance from these ends of the segment being measured so that fringing effects from the source electrodes can be ignored.

It is assumed that the defined regions extend uniformly along the penis so that the current distributes itself in a manner that the voltage drop across the blood and tissue segments are the same, implying that the surface electrode voltage measurement is the same as the voltage throughout the cross section, and in turn allowing for the simple circuit model shown in the drawing. Since the admittance of parallel linear passive elements is the sum of the admittances of the individual elements, the measured admittance is simply the sum of the admittances of the blood and tissue segments. Thus, as shown in FIG. 24, the admittance observed between two electrodes that bound a segment of the penis is simply given by:

$$Y = Y_b + Y_t \tag{1}$$

In general, the admittance Y of a homogeneous region having cross-sectional area A, length L, and resistivity ρ is given by:

$$Y = \frac{A}{\rho \cdot L}$$

and so, in terms of the definitions in Figure 23:

$$Y_b = \frac{A_b}{\rho_b \cdot L} \text{ and } Y_t = \frac{A_t}{\rho_t \cdot L} \tag{2}$$

Substituting equations (2) into (1) gives a general expression for the segment admittance:

$$Y = \left(\frac{A_b}{\rho_b} + \frac{A_t}{\rho_t}\right) \cdot \frac{1}{L} \tag{3}$$

b. Penile length

Now referring to FIG. 20, the fixed distance 310 is designated as $L_F$ and the distance 340 as $L_P$, which is the penile length to be measured. In the context of the section above, electrodes 300 and 305 bound segment 310, and similarly electrodes 300 and 315 bound overlapping segment 340. Using equation (3), the admittance for each segment (designated as $Y_F$ and $Y_P$ respectively) is given by:

$$Y_F = \left(\frac{A_b}{\rho_b} + \frac{A_t}{\rho_t}\right) \cdot \frac{1}{L_F} \tag{4}$$

$$Y_P = \left(\frac{A_b}{\rho_b} + \frac{A_t}{\rho_t}\right) \cdot \frac{1}{L_P} \tag{5}$$

Note here that the blood and tissue regions are assumed to extend uniformly along the length of the penis. The ratio of $Y_F$ to $Y_P$ eliminates the unknown area and resistivity terms and can be rearranged to solve for penile length $L_P$:

$$\frac{Y_F}{Y_P} = \frac{L_P}{Y_F} \tag{6}$$

$$L_p = L_F \cdot \frac{Y_F}{Y_P}$$

Experimental correlation between (6) and physical measurements validates the uniformity assumption.

c. Penile volume change

The volume of the blood and tissue regions of the segment 340 are:

$$V_b = A_b \cdot L_P \text{ and } V_t = A_t \cdot L_P$$

Solving these for the areas and substituting into equation (5) gives:

$$Y_p = \left(\frac{V_b}{\rho_b} + \frac{V_t}{\rho_t}\right) \cdot \frac{1}{L_P^2} \tag{7}$$

Rearranging (7) for the blood volume gives:

$$V_b = \rho_b \cdot \left(L_P^2 \cdot Y_P - \frac{V_t}{\rho_t}\right) \tag{8}$$

In this expression, the length is determined from (6), the admittance is measured, and the blood resistivity is known to be about 135 ohm-cm. However, the tissue volume and resistivity are not known, but assume that the ratio of the two is essentially constant. Now presume two measurements at possibly different lengths are taken. The first measurement could, for example, be a flaccid state measurement, and the second an erect state measurement. The first measurement, denoted with subscript 1, yields:

$$V_{b1} = \rho_b \cdot \left(L_{P1}^2 \cdot Y_{P1} - \frac{V_{t1}}{\rho_{t1}}\right) \tag{9}$$

and the second:

$$V_{b2} = \rho_b \cdot \left(L_{P2}^2 \cdot Y_{P2} - \frac{V_{t2}}{\rho_{t2}}\right) \tag{10}$$

The difference between equations (10) and (11) is the change in blood volume in the segment 340 between states 2 and 1, and is given by:

$$\Delta V_b = \rho_b \cdot (L_{P2}^2 \cdot Y_{P2} - L_{P1}^2 \cdot Y_{P1}) + \varepsilon \tag{11}$$

where:

$$\varepsilon = \rho_b \cdot \left(\frac{V_{t1}}{\rho_{t1}} - \frac{V_{t2}}{\rho_{t2}}\right) \tag{12}$$

A sufficient condition for the error term (12) to be zero is, as mentioned above, that the ratio of the tissue volume to its resistivity be constant. Then (11) does not involve these unknown tissue parameters, i.e.:

$$\Delta V_b = \rho_b \cdot (L_{P2}^2 \cdot Y_{P2} - L_{P1}^2 \cdot Y_{P1}) \tag{13}$$

Constant tissue volume is likely a reasonable assumption, because no new tissue enters the penis as a result of erection (however the tissue volume may change slightly as a result of compression). Also, the resistivity of the tissue is likely a constant parameter related to the type of material, which does not change as a result of erection (again, however, some change may accompany compression of the tissue). Thus, the ratio of these two is likely to be nearly constant. Experiments indicate good correlation between (13) and actual volume changes measured by use of ultrasound.

d. Penile blood volume

Instead of just measuring the change in the blood volume of the penis, absolute volumes could be produced by (8) if the tissue parameters were known or could be estimated. Rewriting (8) so as to separate the tissue terms gives:

$$V_b = \rho_b \cdot L_P^2 \cdot Y_p - \rho_b \cdot \frac{V_t}{\rho_t} \quad (14)$$

The former discussion about the approximate constancy of the ratio of the tissue volume to its resistivity and the known constancy of the blood resistivity imply that the second term is essentially a constant length and volume independent offset.

Rewriting (14) in terms of tissue area yields:

$$V_b = \rho_b \cdot L_P^2 \cdot Y_p - \rho_b \cdot \frac{L_P \cdot A_t}{\rho_t} \quad (15)$$

The flaccid penis is nearly circular, therefore if its radius r is manually measured, the total penile cross-sectional area can be computed as $\pi r^2$. Empirical data indicates that the tissue occupies roughly 80% of this total area, which gives us the ability roughly to estimate the $A_t$ term in (15), using, say, $0.8\ \pi r^2$ as our estimate. (A more accurate, empirically based offset-volume approximation, $V_{os}$, appears below.) The tissue resistivity varies from 300 to 400 ohm-cm in the flaccid state, and so an average value of about 350 ohm-cm could be used in (15), and the blood resistivity has been established to be about 135 ohm-cm.

For the flaccid penis, $L_P$ in equation (15) becomes a constant offset value called $L_{flaccid}$. Therefore, the second term in (15) can be approximated as:

$$V_{os} \approx 135 \cdot \frac{L_{flaccid} \cdot 0.80 \cdot \pi \cdot r^2}{350}, \quad (16)$$

where $V_{os}$ is a constant offset volume. Then the blood volume at any length is approximately given by:

$$V_b = \rho_b \cdot L_P^2 \cdot Y_P - V_{os} \quad (17)$$

Finally, the cross-sectional area of the blood-carrying regions of the penis (primarily the corpora cavernosa) can be determined by dividing this volume estimate by $L_P$. This latter calculation is quite useful is discerning erectile events because, although many effects cause the penis length and volume to change, the cross-section of the blood-carrying vessels increases greatly only as a result of an erection.

Further analysis of the $V_{os}$ variable was performed after obtaining test data from a 16-patient study group. Improved correlation of volume of blood in the penis $V_b$ with a measurement of blood volume by duplex ultrasound was observed after the following modification of $V_{os}$ was applied. Since the anatomy of the penis has dynamically changing components, and since the length of the penis is a dominant dimension of change, $V_{os}$ was modified to be:

$$V_{os} \approx \frac{\rho_b}{\rho_t} \cdot f(L) \cdot L_p \cdot A \quad (65)$$

-continued where $L_p$ is length at the time of measurement. Then $$\frac{dV_{os}}{dL} = \frac{\rho_b}{\rho_t} \cdot A \cdot \frac{\partial f(L)}{\partial L}$$

for $$\frac{\partial f(L)}{\partial L} = \frac{1}{L}$$

$$dV_{os} = \frac{\rho_b}{\rho_t} \cdot A \cdot \frac{dL}{L}$$

$$\Delta V_{os} = \frac{\rho_b}{\rho_t} \cdot A \cdot \ln\left(\frac{L_P}{L_{ref}}\right) + C$$

where $L_{ref}$, or reference length, is the average penis length, in the flaccid state, of the study group.

Figure 41:
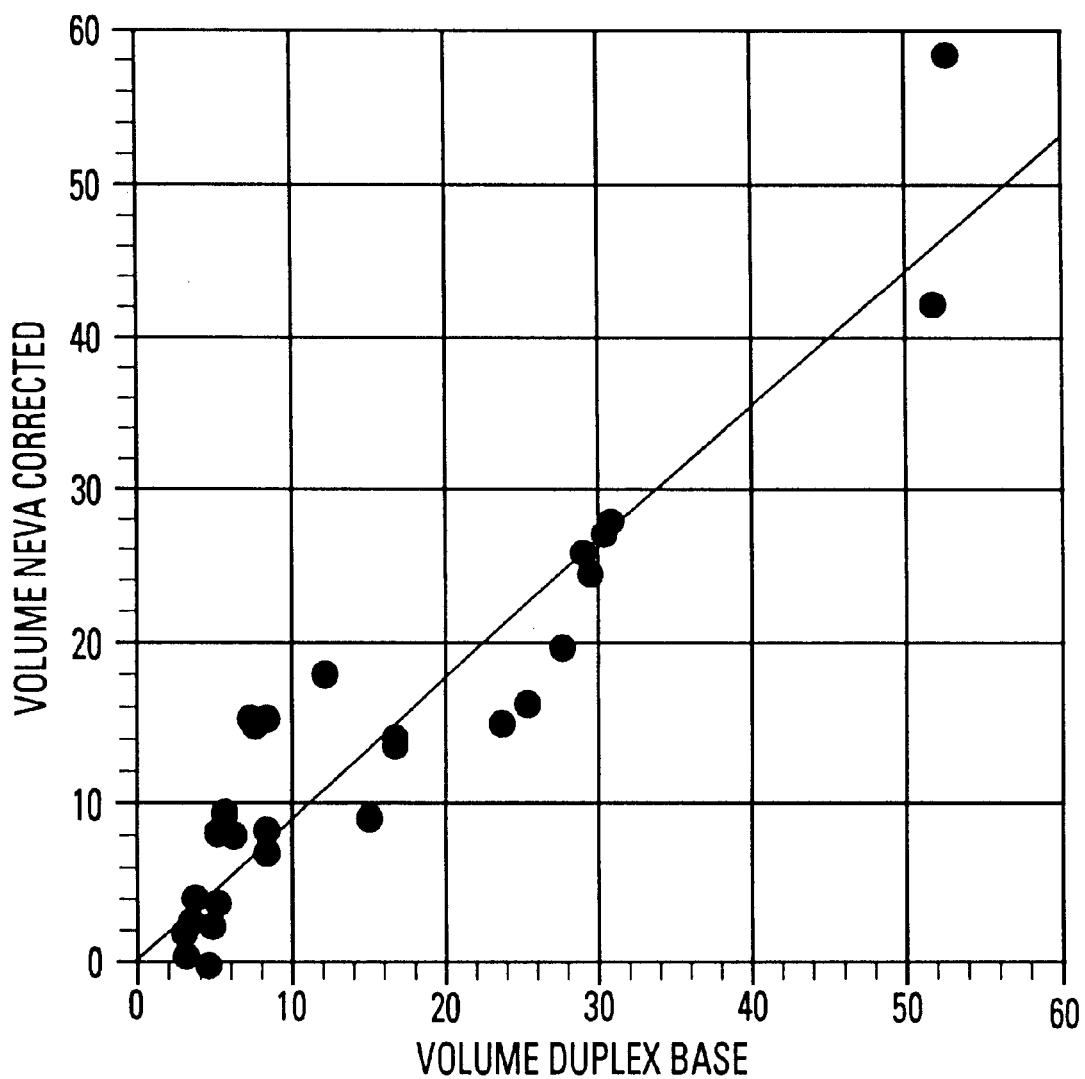
FIG. 41 is a plot showing high correlation between clinical volume measurements taken according to an embodiment of the invention and duplex ultrasound measurements.

From empirically obtained data, the constant of integration, C, can be obtained. Comparison of $V_b$ modified by these relations with $V_b$ from duplex ultrasound measurements demonstrates a high degree of linear correlation with $r^2=0.90$, as shown in FIG. 41. Since $V_{os}$ is length dependent, this additional correction factor improves the correlation.

Thus, in a manner believed heretofore unknown in the prior art, penile variables such as length, volume change, cross-sectional area, and others can be determined using impedance measurements.

10. Derivation Model II

An alternative derivation model is also contemplated according to embodiments of the invention, in which initial penile length is measured directly. There may be certain situations in which this model is beneficial, either in connection with or independently of the previously described derivation model.

a. Penile model

For the purpose of deriving a bioimpedance model of the penis, presume that the penis can be decomposed into two regions filled with homogeneous (in terms of resistivity) material that are, from a circuital standpoint, in parallel. FIGS. 25–26 show the length, cross-sectional area, and resistivity of the two regions as the penis evolves from an initial state (having a known length $L_1$) to a later state, called the "present" state. The regions denoted by the subscripts b and t are the blood- and tissue-filled volumes, respectively, and subscripts 1 and 2 refer to the initial and present states, respectively. Note that the resistivities of the two regions are assumed to be constant.

For purposes of this derivation, then, the following variable definitions apply:

A=Cross sectional area
Y=Admittance
L=Length
ρ=Resistivity
$_{b1}$=Blood in the penis in the initial state.
$_{t1}$=Tissue in the penis in the initial state.
$_{b2}$=Blood in the penis in the present state.
$_{t2}$=Tissue in the penis in the present state.

The total initial and present state volumes, denoted as $V_1$ and $V_2$ respectively, and the implied change in volume $\Delta V$ are given by:

$$V_1 = L_1 \cdot A_{b1} + L_1 \cdot A_{t1}$$

$$V_2 = L_2 \cdot A_{b2} + L_2 \cdot A_{t2}$$

$$\Delta V = V_2 - V_1$$

where the A's are the cross-sectional areas of the respective regions.

Similarly, the admittance of each segment is denoted by $Y_{b1}$ (blood segment, initial), $Y_{t1}$ (tissue segment, initial), $Y_{b2}$ (blood segment, present), and $Y_{t2}$ (tissue segment, present). These admittances are measured by the e.g. thin-electrode contact elements 300, 315 that encompass the areas at the ends of the segment. An alternating current of preferably constant magnitude flows through the total region, and the admittance is measured as the (complex) ratio of this source current to the voltage measured between electrodes 300, 315. The current preferably is applied by electrodes 320, 330 at a sufficient distance from the ends of the segment being measured so that fringing effects from electrodes 320, 330 can be ignored.

b. A First Assumption

It is assumed that the blood- and tissue-filled regions defined above extend uniformly along the penis, i.e. that the magnitudes of the cross-sectional areas of these two regions remain constant along the penis, so that the current distributes itself in a manner that the voltage drop across the blood and tissue segments is the same. This implies that the surface-electrode voltage measurement is the same as the voltage through the cross-section, in turn allowing for the circuit model shown in FIGS. 25–26. Since the admittance (admittance being the inverse of impedance—for purposes of this application, the term impedance value should be interpreted to refer to true impedance or the corresponding admittance) of parallel linear passive elements is the sum of the admittances of the individual elements, the measured admittance is simply the sum of the admittances of the blood and tissue segments. Thus:

$$Y_1 = Y_{b1} + Y_{t1}$$

$$Y_2 = Y_{b2} + Y_{t2}$$

c. Problem Definition

The problem is now defined as finding a means of estimating $\Delta V$ and $L_2$ given the measured admittances $Y_1$ and $Y_2$ and the initial segment length $L_1$. A second assumption is made to effect a solution from this point.

d. The Second Assumption, and Analysis

It is also assumed that the volume of penile tissue does not change with variation in length.

Therefore:

$$A_{t1} \cdot L_1 = A_{t2} \cdot L_2$$

Admittance is generally defined as $$Y = \frac{A}{\rho \cdot L} \text{ for a volume with cross sectional area}$$

A and length L comprised of homogeneous material having resistivity $\rho$, where this admittance is measured from the opposing faces of area A. Therefore, writing $Y_{t1}$ and $Y_{t2}$ in this way and applying the constant-volume assumption yields:

$$Y_{t1} = \frac{A_{t1}}{\rho_t \cdot L_1} \tag{18}$$

-continued $$Y_{t2} = \frac{A_{t2}}{\rho_t \cdot L_2}$$

$$\therefore \frac{Y_{t1}}{Y_{t2}} = \frac{\frac{A_{t1}}{\rho_t \cdot L_1}}{\frac{A_{t2}}{\rho_t \cdot L_2}}$$

$$= \frac{A_{t1} \cdot L_2}{A_{t2} \cdot L_1}$$

$$= \frac{(A_{t1} \cdot L_1) \cdot L_2^2}{(A_{t2} \cdot L_2) \cdot L_1^2}$$

$$= \left(\frac{L_2}{L_1}\right)^2$$

A second ramification of the constant-volume assumption is as follows:

$$\Delta V = V_2 - V_1$$

$$= (L_2 \cdot A_{b2} + L_2 \cdot A_{t2}) - (L_1 \cdot A_{b1} + L_1 \cdot A_{t1})$$

$$= L_2 \cdot A_{b2} - L_1 \cdot A_{b1} \tag{19}$$

Rearranging the expressions for $Y_1$ and $Y_2$ for the blood admittance and applying (18) gives:

$$Y_{b1} = Y_1 - Y_{t1}$$
$$Y_{b2} = Y_2 - Y_{t2}$$
$$Y_{b2} = Y_2 - \left(\frac{L_1}{L_2}\right)^2 \cdot Y_{t1}$$

Now rearranging the $$Y = \frac{A}{\rho \cdot L} \text{ relation as } A = \rho \cdot L \cdot Y \text{ and using the above}$$

expressions, we obtain from (19):

$$\Delta V = \rho_b \cdot \left[ L_2^2 \cdot \left( Y_2 - \left(\frac{L_1}{L_2}\right)^2 \cdot Y_{t1} \right) - L_1^2 \cdot (Y_1 - Y_{t1}) \right] \tag{20}$$

$$= \rho_b \cdot [L_2^2 \cdot Y_2 - L_1^2 \cdot Y_1]$$

Equation (20) relates the change in segment volume to the length $L_2$, which has yet to be determined, and its presence implies that another equation that relates volume and this length is required. To obtain this equation, electrode 305 is located between the two electrodes 300, 315 and spaced at a known fixed distance 310, here represented as $L_F$, from (arbitrarily) electrode 300. The admittance measured along this fixed segment (denoted with the subscript F) follows the earlier development, i.e.:

$$Y_{F1} = Y_{Fb1} + Y_{Ft1}$$

$$Y_{F2} = Y_{Fb2} + Y_{Ft2}$$

where:

$$Y_{Fb1} = \frac{A_{b1}}{\rho_b \cdot L_F}$$

$$Y_{Ft1} = \frac{A_{t1}}{\rho_t \cdot L_F}$$

-continued $$Y_{Fb2} = \frac{A_{b2}}{\rho_b \cdot L_F}$$

$$Y_{Ft2} = \frac{A_{t2}}{\rho_t \cdot L_F}$$

Substituting these into the $Y_{F1}$ and $Y_{F2}$ equations gives:

$$Y_{F1} = \left(\frac{A_{b1}}{\rho_b} + \frac{A_{t1}}{\rho_t}\right) \cdot \frac{1}{L_F}$$

$$Y_{F2} = \left(\frac{A_{b2}}{\rho_b} + \frac{A_{t2}}{\rho_t}\right) \cdot \frac{1}{L_F}$$

Multiplying the first of these by $\rho_t \cdot L_F \cdot L_1$ and the second by $\rho_t \cdot L_F \cdot L_2$ yields:

$$\rho_t \cdot L_F \cdot L_1 \cdot Y_{F1} = \frac{\rho_t \cdot A_{b1} \cdot L_1}{\rho_b} + A_{t1} \cdot L_1$$

$$\rho_t \cdot L_F \cdot L_2 \cdot Y_{F2} = \frac{\rho_t \cdot A_{b2} \cdot L_2}{\rho_b} + A_{t2} \cdot L_2$$

Subtracting the first equation from the second, and applying assumption (18), gives:

$$\rho_t \cdot L_F \cdot (L_2 \cdot Y_{F2} - L_1 \cdot Y_{F1}) = \frac{\rho_t}{\rho_b} \cdot (A_{b2} \cdot L_2 - A_{b1} \cdot L_1)$$

Multiplying both sides by $$\frac{\rho_b}{\rho_t}$$

and noting that the contents of the right-hand parentheses is ΔV from (19) gives:

$$\Delta V = \rho_b \cdot L_F \cdot (L_2 \cdot Y_{F2} - L_1 \cdot Y_{F1}) \qquad (21)$$

Both equations (20) and (21) give ΔV as functions of $L_2$, and equating the right-hand sides of both yields a quadratic in terms of $L_2$ alone. Solving this quadratic for $L_2$ gives:

$$L_2 = \frac{L_F \cdot Y_{F2} + \sqrt{(L_F \cdot Y_{F2})^2 - 4 \cdot L_1 \cdot Y_2 \cdot (L_F \cdot Y_{F1} - L_1 \cdot Y_1)}}{2 \cdot Y_2} \qquad (22)$$

Once $L_2$ has been determined by (22), it can be used in (21) to solve for ΔV.

11. Diagnostic Displays

Figure 27:
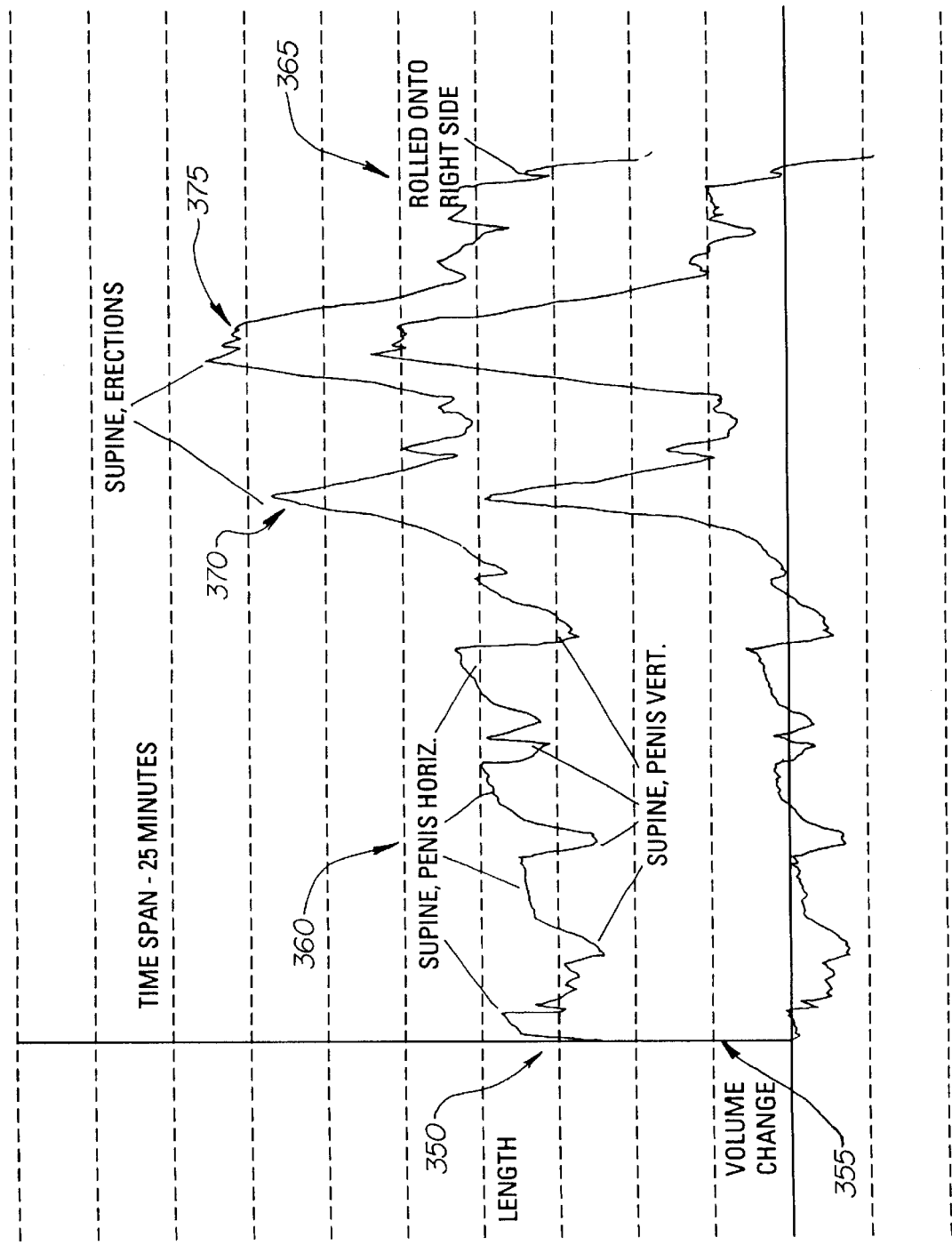
FIG. 27 is a graph showing penile length and blood-volume change data, according to an embodiment of the invention.

Given the penile variable determinations described above, a variety of graphs and other data-display tools can be produced. FIG. 27, for example, is a plot showing length curve 350 and volume-change curve 355, which are based on the measurements and calculations described above. The scale for length curve 350 is 1 cm/division, and the scale for volume-change curve 355 is 10 cc/division. In a manner completely unknown in the prior art, plots such as FIG. 24 can be generated and used in connection with nocturnal penile monitoring to aid in diagnosing organic and/or psychogenic causes of impotence.

As shown in FIG. 27, artifactual effects associated with e.g. patient movement readily can be distinguished from erectile events. Shifting from a penis-horizontal position to a penis-vertical position, for example, is reflected by the relatively small variations in length and volume-change curves 350, 355 in region 360. Similarly, a roll onto the patient's right side is indicated by the distinctive volume-change and length drop-offs in region 365 of FIG. 27.

For erectile events 370, 375, on the other hand, both length curve 350 and volume-change curve 355 show relatively large variations of a characteristic shape, as described further below. Length and volume-change curves 350, 355, therefore, provide double-verification of an erectile event and can be used easily to distinguish erectile events from motion-induced or other artifacts. A simple, unambiguous display or other output tool like that of FIG. 27 allows the medical professional to evaluate patient condition in a straightforward manner, with more numerical data, regarding e.g. length, cross-sectional area and volume, than previously known.

Figure 42:
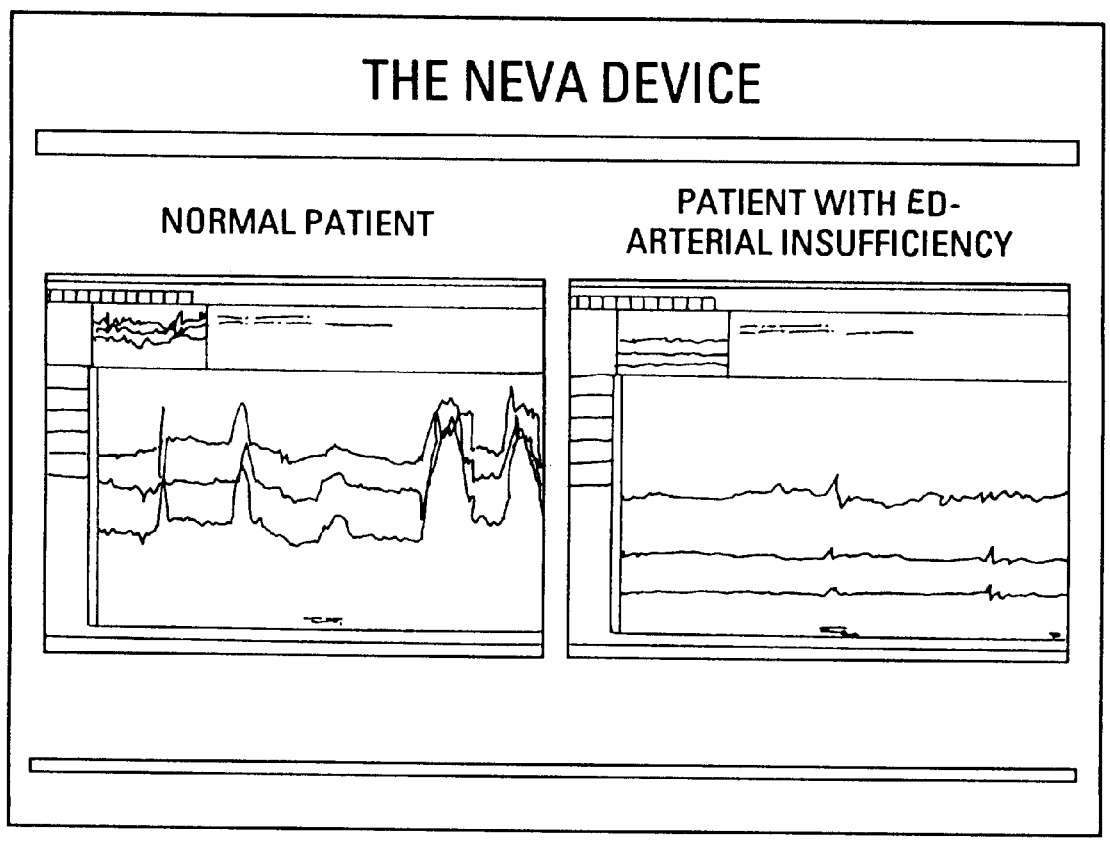
FIGS. 42–43 are easily read displays generated based on clinical data, according to an embodiment of the invention.
Figure 43:
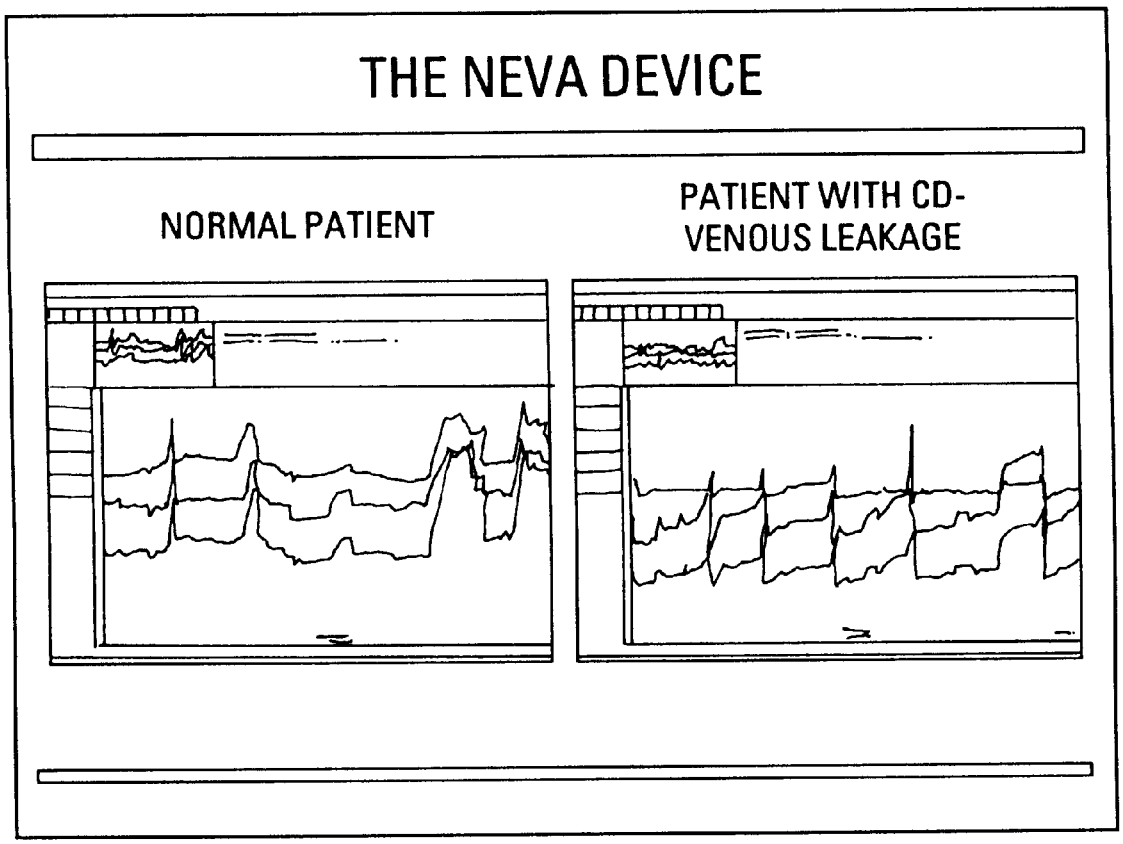

FIGS. 42–43, described below, illustrate actual diagnostic displays from a clinical study.

12. Cardiac-Signature Detection

Further embodiments of the invention will be described with respect to FIGS. 28–34. Here, an impedance waveform is generated using plural electrodes placed in association with the penis as described in previous embodiments. A cardiac signature is detected in the impedance waveform. The cardiac signature is used to detect and appropriately signal an erectile event, readily allowing non-erectile events/artifacts to be distinguished.

Blood courses into the penis during an erectile event in a manner associated with the cardiac cycle. Instead of entering continuously, the blood enters in a pulsatile manner. Given the relationship between penile blood volume and impedance, embodiments of the invention detect a pulsatile component of the impedance waveform and use its existence to indicate the presence of an erectile event. This pulsatile component of impedance, or "cardiac signature," is quite small compared to the magnitude of the impedance, on the order of one one-thousandth of it, but it can be detected and used to signal an erectile event. The cardiac signature can be detected by e.g. applying the impedance waveform to a 0.5 Hz to 10 Hz band-pass filter, which removes the baseline (DC component) and allows the impedance waveform to be scaled up for better visibility.

Figure 28:
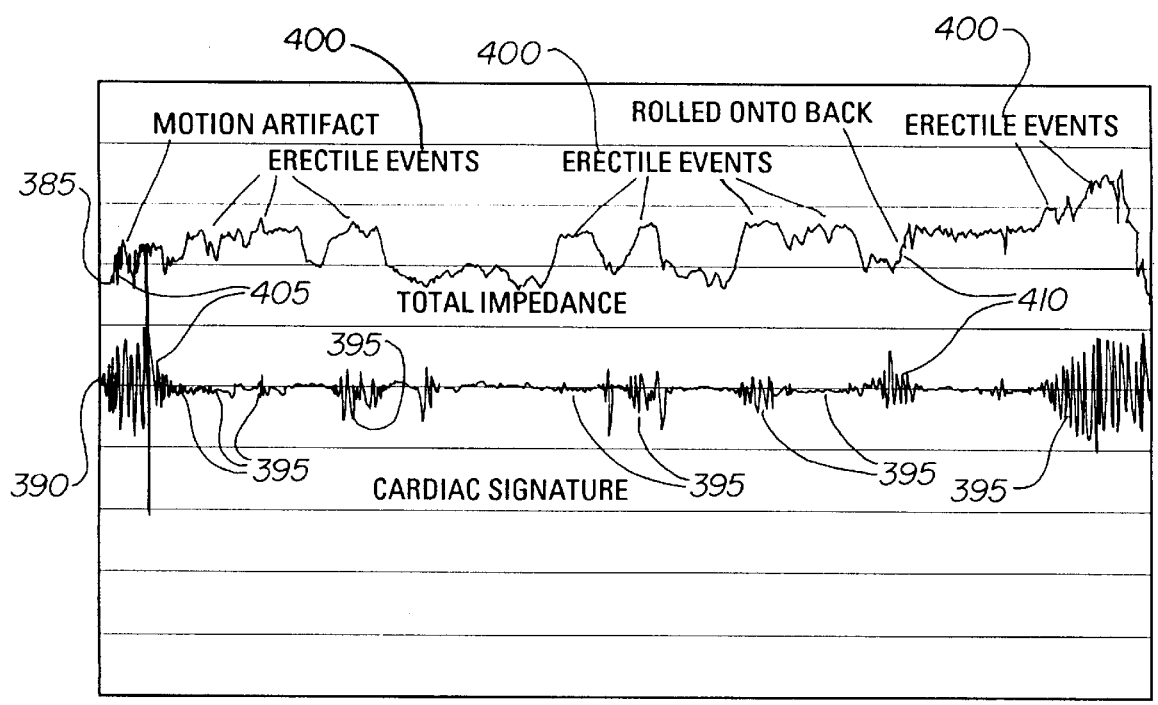
FIG. 28 is a graph showing impedance and cardiac-signature data according to an embodiment of the invention.

FIG. 28 shows both erectile events and non-erectile, artifactual events such as motion or rollover. Total impedance appears as curve 385 and the cardiac signature described above as curve 390. Non-artifact-induced cardiac signature, determined by e.g. computer software in a manner to be described, is indicated at areas 395 of curve 390. These indicate erectile events 400 and can be used to color or shade impedance curve 385 to point out periods of erectile activity. According to one example, curve 385 is primarily blue, but erectile events 400 are indicated in green. Motion artifacts 405, 410 then can readily be distinguished as non-erectile events.

Cardiac signatures that indicate erectile events can be detected e.g. by computer software that recognizes the periodic nature, i.e. the frequency content, of the cardiac signature. A fundamental (e.g., the lowest frequency of a periodically varying quantity) is detected, the frequency of which is proportional to the reciprocal of the period of the waveform. According to one embodiment, the software looks for the existence of a fundamental and a corresponding, relatively small spectral bandwidth as indicative of pulsatile activity associated with an erectile event. Other embodiments can also consider second and potentially third harmonics in performing the analysis.

Figure 29:
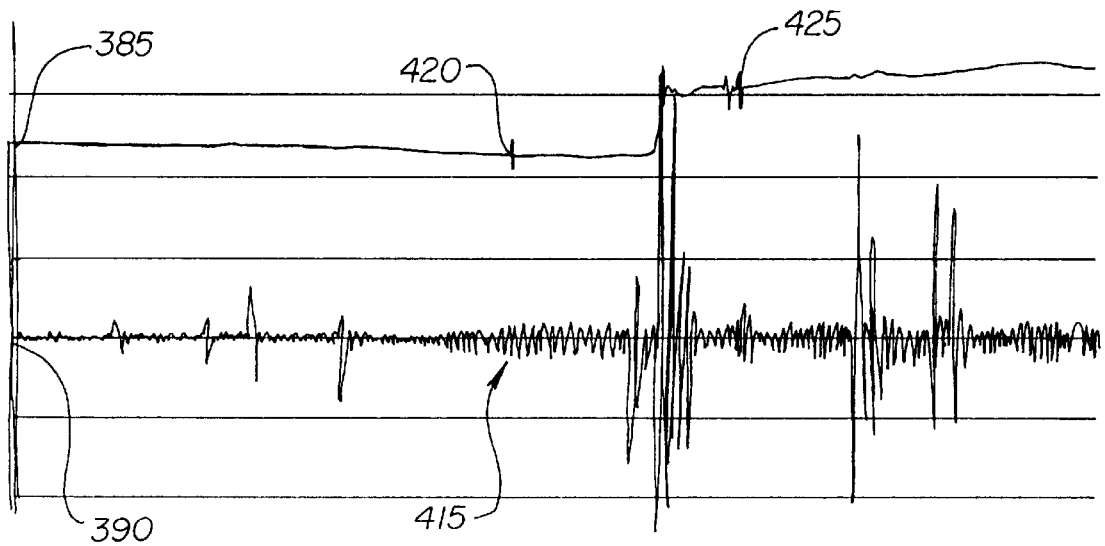
FIGS. 29–30 are detailed views of FIG. 25.

More detailed examples of the analyses possible according to embodiments of the invention are now described with respect to FIGS. 29–34. FIG. 29 is a more detailed, partial view of FIG. 28's impedance waveform 385 and associated cardiac signature 390. FIG. 29 represents a five-minute period of measurement and uses a 50 ohm/division scale for impedance waveform 385 and a 0.5 ohm/division scale for cardiac signature 390. As shown, cardiac signature 390 displays a characteristic pattern in region 415. The existence of cardiac signature 390 in region 415 indicates erectile activity and actually precedes lengthening of the penis by about one minute. The corresponding erectile event is indicated in impedance waveform 385 between start and end points 420, 425 and preferably is highlighted by differential coloring between them. It is believed that as blood flows into the cavernosal arteries during an erectile event, the width of the arteries increases before the length of the penis increases. Region 415 of cardiac signature 390 is believed to represent the pulsatile signal associated with this influx of blood into the cavernosal arteries.

Figure 30:
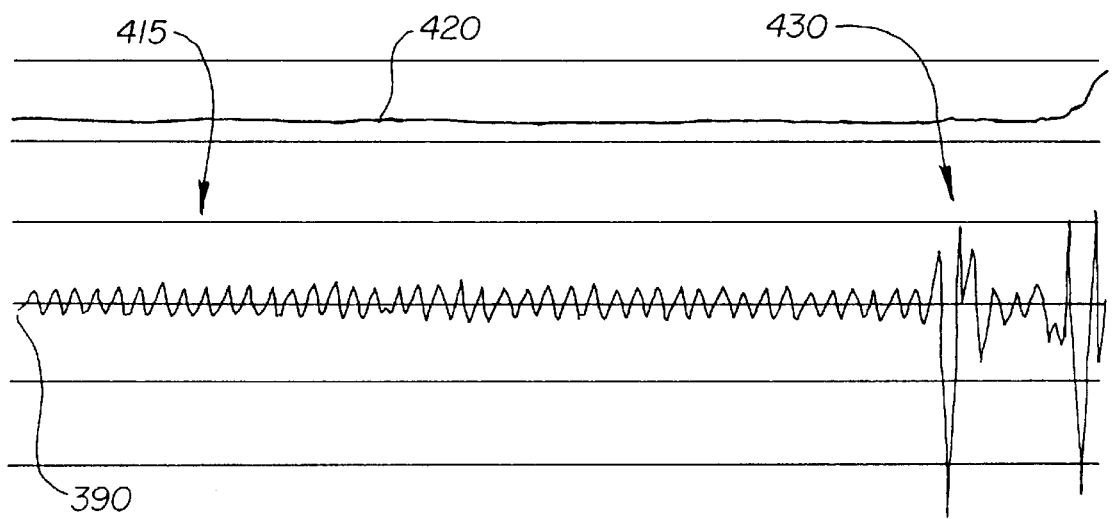

FIG. 30 shows the FIG. 29 data in further detail. Cardiac signature 390 displays a pulsatile component in the one-minute pre-erection period 415, as described above, but also includes larger deflections in region 430. These larger deflections occur as penile length begins to change. The vertical scale for FIG. 30 is the same as for FIG. 29.

Figure 31:
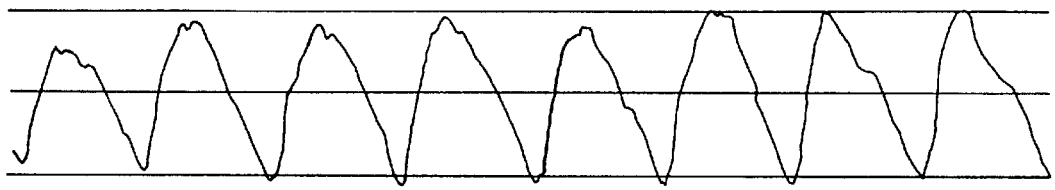
FIGS. 31–34 show inverted impedance cardiac data, according to an embodiment of the invention.
Figure 32:
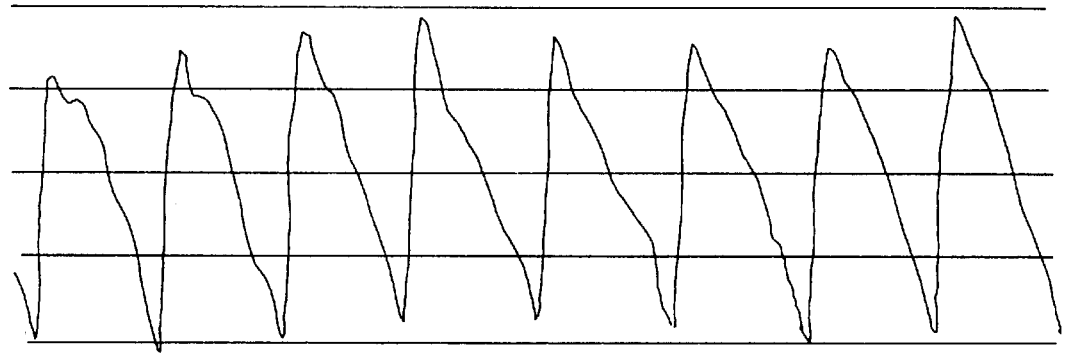
Figure 33:
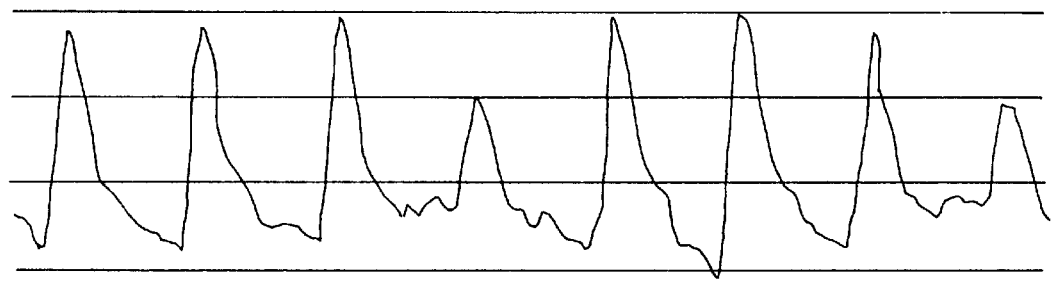
Figure 34:

FIGS. 31–34 show inverted cardiac impedance data over approximately eight-second periods, with a vertical scale of 0.1 ohm/division. FIG. 31 shows the pre-erection period, in region 415 of FIG. 29. FIG. 32 shows the time of full erection in FIG. 29. FIG. 33 shows a time near the end of the erection in FIG. 29, when venous outflow is increased as the erection subsides. Finally, for comparison purposes, FIG. 34 shows data derived from a radial artery in the arm.

Cardiac-signature analysis, including analysis of cardiac-signature amplitude, according to the invention can be used with the various embodiments described herein, including the two-electrode, four-electrode and five-electrode embodiments.

13. Correlation of Cardiac Signature to Etiology

Significantly, the venous outflow at the end of the erection causes a distinctive cardiac signature, as shown in FIG. 33. According to embodiments of the invention, therefore, cardiac-signature shape can be used as a template to diagnose a particular cause of organic impotence. For example, if the cardiac signature indicates increased venous outflow in a manner akin to FIG. 30 but at the beginning of an erection, instead of at the end, venous leakage likely is occurring.

Thus, much like clinicians can memorize cardiac ECG templates associated with various states of disease, cardiac-signature templates according to the invention can be used in determining particular impotence etiologies. Arterial disease can be indicated by cardiac signatures of reduced magnitudes, for example, potentially because the distensibility of the relevant blood vessels is compromised. Arterial deficiency can also be indicated by reduced or non-existent increases in cardiac signature, in combination with reduced or non-existent increases in blood volume. Venous leakage can be diagnosed if, for example, cardiac signature increases normally in association with an erectile event, but blood-volume level does not. Thus, etiology of organic impotence versus psychogenic impotence, as well as the type of organic impotence, can be determined.

14. Cardiac Signature—Background Discussion

Figure 35:
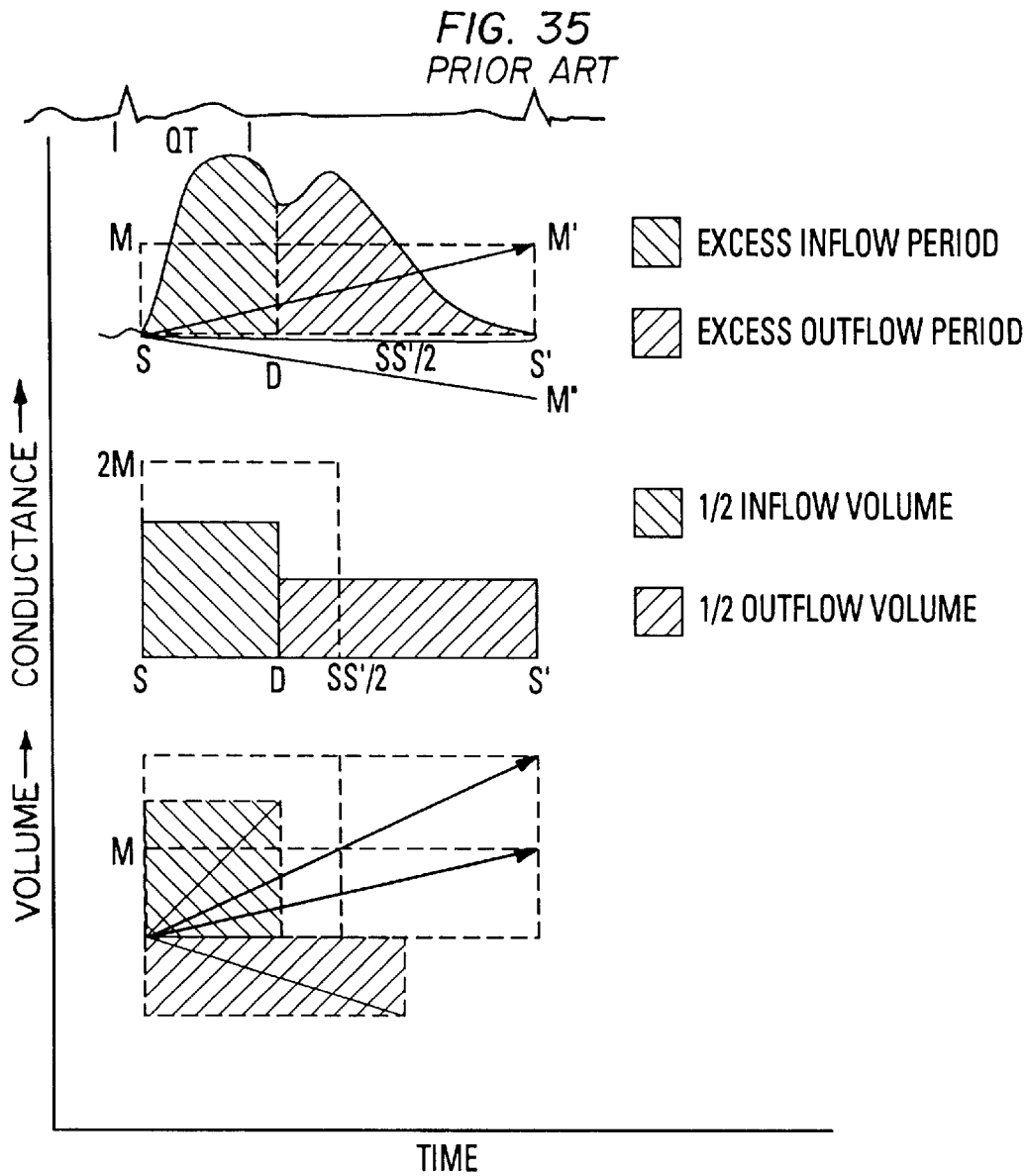
FIGS. 35–40 show pulse-volume and pulse-waveform analyses according to the prior art.

FIG. 1 of the above-mentioned 1970 Nyboer reference is reproduced as FIG. 35 herein and shows one concept of volume pulse. Nyboer states that as much blood runs out of a particular bodily segment as into it during a complete pulse cycle, under normal circumstances. The area under the pulse curve can also be represented by the mean height (M) over the length SS' for the cycle. Twice the summated area (2 M×SS'/2) expresses the surplus arterial volume per cycle within the segment if the venous outflow was occluded. FIG. 35 also shows how the duration of excess input (S-D) and excess output (D-S') may be approximated planimetrically.

Figure 36:
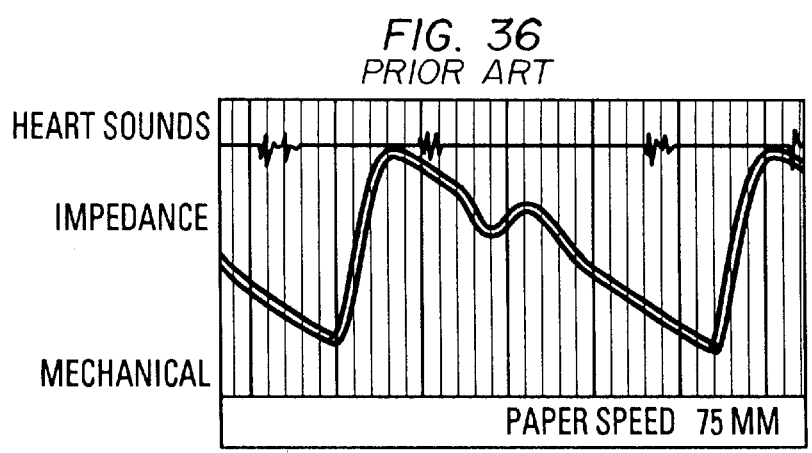

Nyboer also states that the mechanical origin of the electrical impedance pulse can be identified synchronously by a mechanical plethysmograph. To that end, FIG. 36 represents a synchronous study of a mechanical and electrical impedance pulsation derived from a finger segment. Nyboer concluded that quantitative blood-volume values could be found from the pulse curve, if certain assumptions were made. Most importantly, the assumption was made that the measured change in conductivity is an accurate index of volume.

Figure 37:
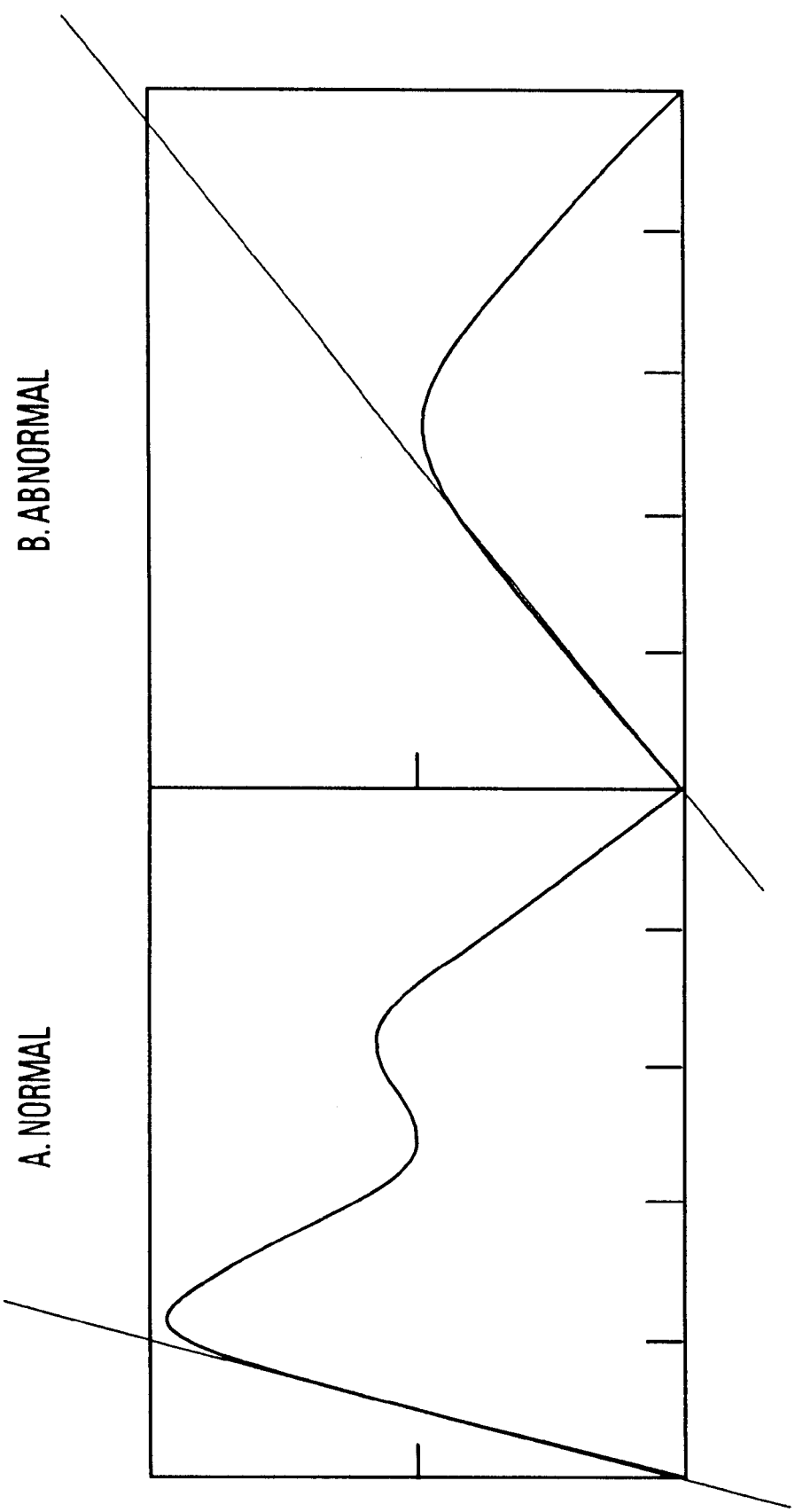
Figure 38:
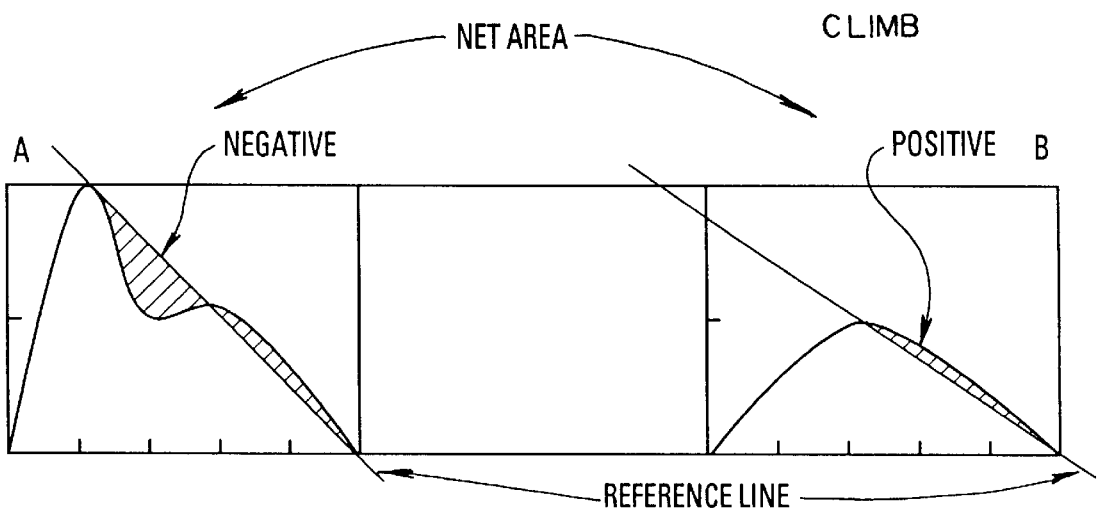
Figure 39:
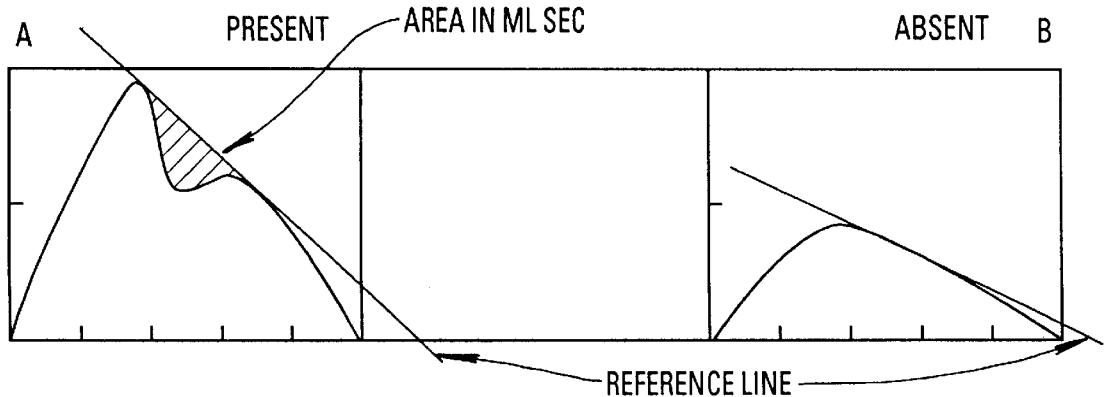
Figure 40:
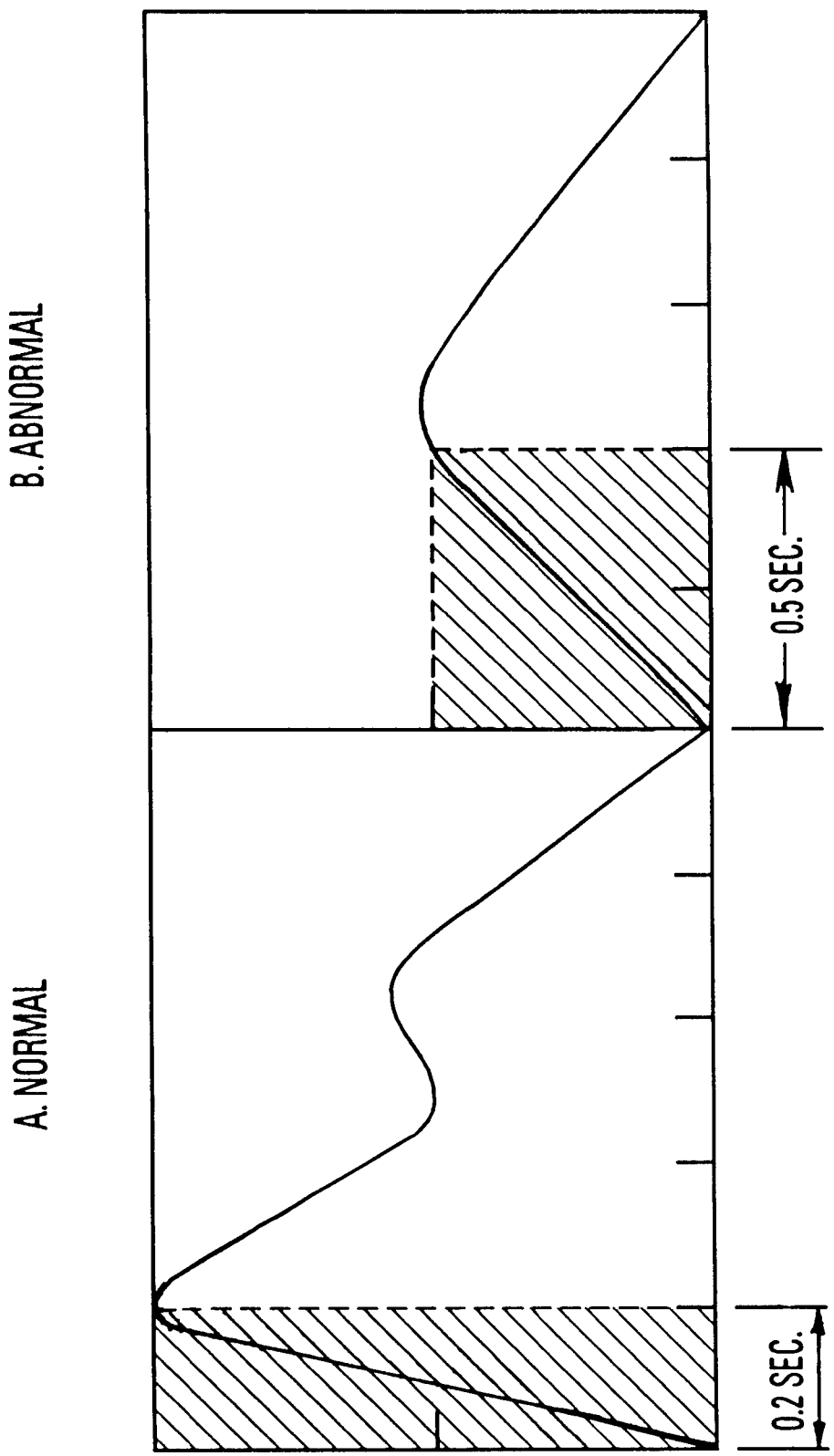

The above-mentioned Kedia reference used penile-cuff occlusion to generate and compare pulse waveforms from potent and impotent males. A normal pulse waveform features a sharp rise in the anacrotic limb (systolic upstroke) (FIG. 37), a rapid fall of the catacrotic limb to the baseline (diastolic downslope) (FIG. 38), and a dicrotic notch on the catacrotic limb (FIG. 39). As seen in FIG. 40, Kedia indicated that crest time is a measurement from the base to the peak of the pulse wave. In normal males, crest time should not exceed 35% of the total cycle length. Kedia provided a good basis for understanding the qualitative nature of a normal pulse waveform. Kedia did not provide formulas and/or calculations for actual use, however.

15. Clinical Data

FIG. 41 shows a high degree of correlation between clinically obtained volume measurements according to an embodiment of the invention and duplex ultrasound measurements, as explained above in section 9, entitled Derivation Model I.

FIGS. 42–43 show four data displays based on clinical tests using human patients. For each display, the uppermost display curve represents penile cross-sectional area, the middle curve penile length and the lower curve penile volume, in a graphical manner similar to that of e.g. FIG. 27. In both FIGS. 42 and 43, graphical data from a patient without symptoms of impotence are displayed on the left side. Erectile events are readily discernible, based on the substantially consistent tracking of the length, volume and cross-sectional area curves.

The right side of FIG. 42 shows data for a patient with known erectile dysfunction due to arterial insufficiency. The fewer number and lesser height of the peaks in the displayed curves show this clearly. FIG. 43, in contrast, shows data for a patient with known erectile dysfunction due to venous leakage. Although there are peaks of substantial height, it is easy to discern from the display that they drop off very quickly—evidence of venous leakage. In this regard, these peaks are similar to the venous-leakage characteristic peak shown in FIG. 6.

As is clear from FIGS. 42–43, the graphical display features of the invention are a powerful tool for analyzing erectile activity and diagnosing erectile dysfunction. As needed, certain areas of the displayed curves can be enlarged or otherwise brought into more detailed view for closer analysis.

16. Conclusion

Embodiments of the invention provide data useful for distinguishing erectile events from motion-induced and other artifacts, data that is far more accurate and reliable than heretofore obtainable. Embodiments of the invention thus obtain extremely useful information in determining the etiology of erectile dysfunction, including information useful to distinguish different forms of organic impotence.

Additionally, embodiments of the invention provide far more data than previously has been available in nocturnal penile monitoring situations. Instead of being merely an "erection detector," embodiments of the invention provide detailed data regarding the changing penile length, blood volume and other variables. Data concerning the magnitude of any potential organic causes also is obtained, e.g. the degree of venous leakage. These data effectively can be used to titrate dosages of appropriate medication far more accurately than previously known, without a trial-and-error approach. Thus underdosage and consequent patient frustration, and overdosage and consequent embarrassment or harmful effect, can be substantially reduced if not avoided entirely.

According to the various embodiments of the invention, nocturnal erectile events can be recorded, downloaded and displayed with far greater precision, accuracy, patient ease and patient comfort than heretofore known. Whereas prior art devices have often failed to reveal much useful information regarding the mechanisms of erectile dysfunction, embodiments of the invention provide detailed information over an extended period of time. Based on graphical or other data displays, the medical professional has the ability to diagnose insufficient arterial inflow, excessive venous leakage, or a mixed vascular etiology. Alternatively, purely psychogenic dysfunction can also be diagnosed and appropriate treatment recommended. The effects of long-term treatment therapies, in connection with e.g. smoking cessation, drug therapy, counseling, etc., can also be quantified and documented. Significantly, penile variables such as length values, volume values, cross-sectional area values and volume-filling values are effectively determined or estimated, providing far more information than available in the prior art. Information concerning the duration and number of erectile events is also available for display and/or analysis.

Embodiments of the invention provide a number of additional advantages. In addition to being far more comfortable, compact and therefore more portable than many prior art devices, embodiments of the invention consume far less battery power and may allow the medical professional to apply and secure the electrodes instead of the patient. Artifactual effects are minimized. The invention in its preferred embodiments need not be disconnected for urination. Additionally, embodiments according to the invention measure and display continuously over an extended period of time, and software or an operator can look for and hone in on specific erectile events in question. Display windows showing those events then can be opened and viewed by the medical professional and even by the patient, which can provide additional reassurance to the patient. Further, embodiments of the invention require less apparatus to be supported directly on the penis. The invention also eliminates the motor-induced tugging/constricting effect necessary in certain other devices, which can perturb or even abort the erectile event due to its perceived invasive effect on the patient.

While the invention has been described with respect to certain preferred embodiments, the invention should not be considered limited to those embodiments. For example, the features described above with respect to individual figures generally can be used with features of other figures as desired to suit a particular application. Various other modifications and changes will be evident to those of ordinary skill.

What is claimed is:

1. A method of monitoring the tumescent state of the penis of a patient, the method comprising:

(a) placing sensing elements in proximity to the penis;

(b) sensing impedance values of the penis both when the penis is in an erect state and when the penis is in a flaccid state with the sensing elements;

(c) determining at least one penile variable using the impedance values, the at least one penile variable being selected from the group consisting of length, volume, volume-change, and volume-filling rate variables; and (d) using the at least one penile variable to generate a display output.

2. The method of claim 1, wherein (a) includes placing at least five sensing elements in proximity to the penis.

3. The method of claim 2, wherein the sensing elements are contact electrodes.

4. The method of claim 2, wherein at least four of the sensing elements are supported on the penis.

5. The method of claim 4, wherein at least two of the sensing elements are supported in the base region of the penis, said at least two sensing elements being separated by a substantially fixed separation distance.

6. The method of claim 5, wherein at least two other sensing elements are supported in the tip region of the penis, one of the at least two sensing elements being supported subcoronally, the subcoronal sensing element being used to determine penile length values in (c).

7. The method of claim 1, wherein (b) includes sensing impedance values in at least two regions of the penis, the first region being a base region and the second region extending from substantially within the base region to substantially a tip region of the penis.

8. An apparatus for monitoring the tumescent state of the penis of a patient, the apparatus comprising:

a plurality of sensing elements to be placed in proximity to the penis for sensing impedance values of the penis both when the penis is in an erect state and when the penis is in a flaccid state;

a processing device operably coupled to the plurality of sensing elements, the processing device determining at least one penile variable using the impedance values, the at least one penile variable being selected from the group consisting of length, volume, volume-change, and volume-filling rate variables; and an output device operably coupled with the processing device to generate a display using the at least one determined penile variable.

9. The apparatus of claim 8, wherein the output device displays a plot of penile length and penile volume values for comparison by a user of the apparatus.

10. The apparatus of claim 8, wherein the output device displays a plot of penile length and penile volume values, the plot allowing a user of the apparatus readily to distinguish artifactual effects from erectile events.

11. The apparatus of claim 8, wherein at least two of the sensing elements are supported by the base region of the penis and separated by a distance that remains substantially fixed.

12. The apparatus of claim 8, wherein the sensing elements sense impedance values of the penis both in a base region and along substantially an entire effective length of the penis.

13. The apparatus of claim 8, wherein the plurality of sensing elements comprises at least five sensing elements.

14. The apparatus of claim 8, wherein at least two of the sensing elements are supported in the base region of the penis and at least two of the sensing elements are supported in the tip region of the penis.

15. The apparatus of claim 14, wherein at least one of the sensing elements is supported off the penis.

16. The apparatus of claim 15, wherein the at least one sensing element supported off the penis is supported in the hip region of the patient.

17. The apparatus of claim 8, wherein the processing device approximates change in an offset volume variable according to the equation:

$$\Delta V_{os} = \frac{\rho_b}{\rho_t} \cdot A \cdot \ln\left(\frac{L_P}{L_{ref}}\right) + C$$

where $\Delta V_{os}$ is change in offset volume, $\rho_b$ and $\rho_t$ are resistivities of blood and tissue filled penile volumes, respectively, A is cross-sectional area, $L_P$ is penile length at the time of measurement, $L_{ref}$ is a reference length reflecting average length of the penis in the flaccid state, and C is an integration constant.

18. An apparatus for monitoring the tumescent state of the penis of a patient, the apparatus comprising a plurality of sensing elements to be placed in proximity to the penis for sensing impedance values of the penis both when the penis is in an erect state and when the penis is in a flaccid state, the plurality of sensing elements being operably couplable to a processing device for determining penile variables using the impedance values, the penile variables being suitable for display by an output device.

19. The apparatus of claim 18, wherein the penile variables are used to determine dosage levels of oral or other impotence medication.

20. The apparatus of claim 18, wherein the plurality of sensing elements include a plurality of on-penis electrodes and at least one off-penis electrode.

21. The apparatus of claim 18, wherein the plurality of sensing elements include a first electrode in a base region of the penis, a second electrode in a base region of the penis and spaced from the first electrode, and a third electrode in a distal region of the penis, further wherein the apparatus measures voltage drop between (1) the first electrode and the second electrode and between (2) the first electrode and the third electrode.

22. The apparatus of claim 18, wherein the plurality of sensing elements are used to determine penile length variables over time.

23. The apparatus of claim 18, wherein the plurality of sensing elements are used to determine information reflecting changing width of a cavernosal blood vessel in the penis of the patient substantially before the length of the penis changes during an erectile event.

24. The apparatus of claim 18, wherein the plurality of sensing elements are used to determine cardiac signature data to indicate periods of penile activity.

25. The apparatus of claim 24, wherein the cardiac signature data is used as a template for diagnosis of organic impotence etiology.

26. The apparatus of claim 18, further comprising a data storage device operably coupled to the sensing elements for receiving and storing penile impedance values of the penis and for optional subsequent downloading.

27. The apparatus of claim 18, wherein the processing device approximates change in an offset volume variable according to the equation:

$$\Delta V_{os} = \frac{\rho_b}{\rho_t} \cdot A \cdot \ln\left(\frac{L_P}{L_{ref}}\right) + C$$

where $\Delta V_{os}$ is change in offset volume, $\rho_b$ and $\rho_t$ are resistivities of blood and tissue filled penile volumes, respectively, A is cross-sectional area, $L_P$ is penile length at the time of measurement, $L_{ref}$ is a reference length reflecting average length of the penis in the flaccid state, and C is an integration constant.

28. The apparatus of claim 26, wherein the data storage device is constructed to be secured to the patient's leg.

29. A method of monitoring the tumescent state of the penis of a patient, the method comprising:

(a) determining impedance values of the penis;

(b) determining cardiac-signature data using the penile impedance values; and (c) using the cardiac-signature data to indicate periods of penile activity.

30. The method of claim 29, wherein (b) includes determining a pulsatile component of an impedance waveform, the waveform being based on the impedance values determined in (a).

31. The method of claim 29, further including (d) displaying the cardiac-signature data in graphical form to evaluate potential organic causes of erectile dysfunction.

32. The method of claim 29, wherein (c) includes recognizing cardiac-signature activity that occurs before the penis lengthens during an erectile event.

33. An apparatus for monitoring the tumescent state of the penis of a patient, the apparatus comprising:

apparatus for determining impedance values of the penis;

apparatus for determining cardiac-signature data using the penile impedance values; and apparatus for indicating periods of penile activity using the cardiac-signature data.

34. The apparatus of claim 33, further comprising apparatus for displaying at least cardiac-signature data in graphical form.

35. The apparatus of claim 34, wherein the displaying apparatus further displays total impedance data, the displayed total impedance data being highlighted during corresponding periods of cardiac-signature activity to reflect potential erectile events.

36. The apparatus of claim 33, further comprising apparatus for displaying impedance-based data in graphical form, the impedance-based data being highlighted during selected periods of cardiac-signature activity to reflect potential erectile events.

37. An apparatus for nocturnally monitoring erectile events in a patient, the apparatus comprising:

sensing apparatus for sensing penile data over time while the patient is asleep; and display apparatus for displaying information determined from the penile data versus time;

wherein the displayed information is used to diagnose vasculogenic and/or psychogenic causes of erectile dysfunction;

wherein the sensing apparatus is used to determine penile-tissue impedance values and blood impedance values.

38. The apparatus of claim 37, wherein the displayed information is in graphical form and is used to evaluate the relative speed of erection-impairing venous leakage.

39. The apparatus of claim 37, wherein the penile-tissue impedance values and blood impedance values are determined substantially continuously over time.

40. The apparatus of claim 30, wherein a diurnal erectile event is medicinally induced in a flaccid penis while the patient is awake;

the sensing apparatus senses diurnal penile data during said diurnal erectile event; and the display apparatus facilitates comparison of nocturnal penile data with diurnal penile data to evaluate the quality of nocturnal erectile events.

41. The apparatus of claim 40, wherein the diurnal erectile event is medicinally induced in a medical professional's office, further wherein the sensing apparatus senses the diurnal penile data in the patient's usual sleep location.

42. An apparatus for nocturnally monitoring erectile events in a patient, the apparatus comprising:
sensing apparatus for sensing penile data over time while the patient is asleep; and
display apparatus for displaying information determined from the penile data versus time;
wherein the displayed information is used to diagnose vasculogenic and/or psychogenic causes of erectile dysfunction;
further wherein the apparatus approximates change in an offset volume variable according to the equation:

$$\Delta V_{os} = \frac{\rho_b}{\rho_t} \cdot A \cdot \ln\left(\frac{L_P}{L_{ref}}\right) + C$$

where $\Delta V_{os}$ is change in offset volume, $\rho_b$ and $\rho_t$ are resistivities of blood and tissue filled penile volumes, respectively, A is cross-sectional area, $L_P$ is penile length at the time of measurement, $L_{ref}$ is a reference length reflecting average length of the penis in the flaccid state, and C is an integration constant.

43. An apparatus for monitoring the tumescent state of the penis of a patient, the apparatus comprising means for sensing impedance values of the penis both when the penis is in an erect state and when the penis is in a flaccid state, the means for sensing to be placed in proximity to the penis, the means for sensing being operably couplable to means for processing, the means for processing determining penile variables using the impedance values, the penile variables being suitable for display by an output device.

44. The apparatus of claim 43, the means for sensing comprising at least five sensing elements.

45. The apparatus of claim 43, wherein the output device displays a plot of penile length and penile volume variables for comparison by a user of the apparatus.

46. A method of monitoring the tumescent state of the penis of a patient, the method comprising:
(a) placing at least five sensing elements in proximity to the penis;
(b) sensing penile impedance values with the sensing elements;
(c) determining at least one penile variable using the impedance values, the at least one penile variable being selected from the group consisting of length, volume, volume-change, cross-sectional area and volume-filling rate variables; and
(d) using the at least one penile variable to generate a display output.

47. An apparatus for monitoring the tumescent state of the penis of a patient, the apparatus comprising a plurality of sensing elements to be placed in proximity to the penis for sensing penile impedance values, the plurality of sensing elements being operably couplable to a processing device for determining penile variables using the impedance values, the penile variables being suitable for display by an output device, wherein the processing device approximates change in an offset volume variable according to the equation:

$$\Delta V_{os} = \frac{\rho_b}{\rho_t} \cdot A \cdot \ln\left(\frac{L_P}{L_{ref}}\right) + C$$

where $\Delta V_{os}$ is change in offset volume, $\rho_b$ and $\rho_t$ are resistivities of blood and tissue filled penile volumes, respectively, A is cross-sectional area, $L_P$ is penile length at the time of measurement, $L_{ref}$ is a reference length reflecting average length of the penis in the flaccid state, and C is an integration constant.

48. An apparatus for nocturnally monitoring erectile events in a patient, the apparatus comprising:
sensing apparatus for sensing penile data over time while the patient is asleep; and
display apparatus for displaying information determined from the penile data versus time;
wherein the displayed information is used to diagnose vasculogenic and/or psychogenic causes of erectile dysfunction;
further wherein:
a diurnal erectile event is medicinally induced in a flaccid penis while the patient is awake;
the sensing apparatus senses diurnal penile data during said diurnal erectile event; and
the display apparatus facilitates comparison of nocturnal penile data with diurnal penile data to evaluate the quality of nocturnal erectile events.

49. The apparatus of claim 48, further comprising processing apparatus physically distinct from the sensing apparatus and the display apparatus for processing the penile data.

* * * * *